US010578628B2

(12) United States Patent
Ieko et al.

(10) Patent No.: US 10,578,628 B2
(45) Date of Patent: Mar. 3, 2020

(54) METHOD FOR ACQUIRING INFORMATION ON CAUSE OF PROLONGATION OF COAGULATION TIME, AND DEVICE

(71) Applicants: SCHOOL JURIDICAL PERSON HIGASHI-NIPPON-GAKUEN, Ishikari-gun, Hokkaido (JP); SYSMEX CORPORATION, Kobe-shi, Hyogo (JP)

(72) Inventors: Masahiro Ieko, Hokkaido (JP); Osamu Kumano, Kobe (JP); Haruki Yamaguchi, Kobe (JP); Takeshi Suzuki, Kobe (JP)

(73) Assignees: SYSMEX CORPORATION (JP); SCHOOL JURIDICAL PERSON HIGASHI-NIPPON-GAKUEN (JP)

( * ) Notice: Subject to any disclaimer, the term of this patent is extended or adjusted under 35 U.S.C. 154(b) by 174 days.

(21) Appl. No.: 15/686,976

(22) Filed: Aug. 25, 2017

(65) Prior Publication Data
US 2017/0350907 A1    Dec. 7, 2017

Related U.S. Application Data

(63) Continuation of application No. PCT/JP2016/054599, filed on Feb. 17, 2016.

(30) Foreign Application Priority Data

Feb. 27, 2015    (JP) ................... 2015-039006

(51) Int. Cl.
*G01N 33/86*    (2006.01)
*G01N 33/49*    (2006.01)
(Continued)

(52) U.S. Cl.
CPC ............. *G01N 33/86* (2013.01); *G01N 21/82* (2013.01); *G01N 33/4905* (2013.01);
(Continued)

(58) Field of Classification Search
CPC ...... G01N 21/272; G01N 21/51; G01N 21/82; G01N 33/86; G01N 33/49; G01N 33/4905; G01N 35/025; G16H 50/20
(Continued)

(56) References Cited

U.S. PATENT DOCUMENTS

| 10,215,766 B2* | 2/2019 | Shima .................... G01N 33/86 |
| 2011/0129862 A1* | 6/2011 | Nakamura ............. G01N 33/86 |
| | | 435/13 |

(Continued)

FOREIGN PATENT DOCUMENTS

| EP | 2290370 A1 | 3/2011 |
| EP | 2508891 A1 | 10/2012 |
| EP | 2775292 A1 | 9/2014 |

OTHER PUBLICATIONS

Kumano et al. Thrombosis Research, vol. 143, May 10, 2016, pp. 53-57.*

(Continued)

*Primary Examiner* — Maureen Wallenhorst
(74) *Attorney, Agent, or Firm* — Brinks Gilson & Lione

(57) ABSTRACT

The present invention relates to a method for acquiring information on a cause of prolongation of coagulation time. The present invention also relates to a device, a system and a computer program for analyzing blood coagulation.

11 Claims, 20 Drawing Sheets

(51) Int. Cl.
  *G01N 35/02* (2006.01)
  *G01N 21/82* (2006.01)
  *G16H 50/20* (2018.01)
  *G01N 21/27* (2006.01)
  *G01N 21/51* (2006.01)

(52) U.S. Cl.
  CPC .......... *G01N 35/025* (2013.01); *G16H 50/20* (2018.01); *G01N 21/272* (2013.01); *G01N 21/51* (2013.01)

(58) Field of Classification Search
  USPC .............. 436/63, 69, 164; 435/13; 73/64.41, 73/64.43; 600/369
  See application file for complete search history.

(56) References Cited

U.S. PATENT DOCUMENTS

2016/0291041 A1* 10/2016 Kumano .............. G01N 33/564
2018/0080948 A1*  3/2018 Yabutani ................ G01N 21/82
2018/0356433 A1* 12/2018 Kumano ................ G01N 33/86

OTHER PUBLICATIONS

Kumano et al. Journal of Thrombosis and Haemostasis, vol. 11, 2013, pp. 1919-1922.*
Collins, P. et al., "Consensus Recommendations for the Diagnosis and Treatment of Acquired Hemophilia A", *BMC Research Notes*, vol. 3, No. 161, 2010, 8 pages.
Naito, S. et al., "Evaluation and Usefulness of LA Detection b New Determination Method for Cross Mixing Test", *Medical Online*, 2012, 4 pages (with English language translation).
Pengo, V. et al., "Update of the Guidelines for Lupus AntiCoagulant Detection", *Journal of the Thrombosis and Haemostasis*, vol. 7, pp. 1737-1740.
Kumano et al., "Verification of the guidelines for lupus anticoagulant detection: Usefulness of index for circulating anticoagulant in APTT mixing test" Thrombosis Research 134 (2014) 503-509, published online May 29, 2014.
Kershaw et al., "Mixing Tests: Diagnostic Aides in the Investigation of Prolonged Prothrombin Times and Activated Partial Thromboplastin Times" Seminars in Thrombosis & Hemostasis, vol. 39, No. 3/2013 (2013) 283-290, published online Mar. 2, 2013.
Communication pursuant to Article 94(3) EPC in Europe Application No. 16755305.6, dated Jan. 22, 2020, 5 pages.
Office Action in Japan Application No. 2017-502297, dated Jan. 14, 2020, including English translation, 7 pages.

* cited by examiner

Fig. 11B

METHOD FOR ACQUIRING INFORMATION ON CAUSE OF PROLONGATION OF COAGULATION TIME, AND DEVICE

RELATED APPLICATIONS

This application is a continuation application of PCT/JP2016/054599, filed Feb. 17, 2016, which claims the benefit of the filing date pursuant to 35 U.S.C. § 119(e) of JP2015-039006, filed Feb. 27, 2015, all of which are incorporated herein by reference.

BACKGROUND OF THE INVENTION

1. Field of the Invention

The present invention relates to a method for acquiring information on a cause of prolongation of coagulation time. The present invention also relates to a device, a system and a computer program for analyzing blood coagulation.

2. Description of the Related Art

The coagulation test, which is one of blood tests, is performed by measuring coagulation time of blood, for grasping the state of hemostatic mechanism. When prolongation of coagulation time is observed, congenital coagulation disorder caused by congenital deficiency or abnormality of blood coagulation factor or acquired coagulation inhibition caused by autoantibody inhibiting coagulation reaction is suspected as the cause. Congenital coagulation disorder and acquired coagulation inhibition can be differentiated by a test that measures coagulation time of a sample obtained by mixing test plasma showing prolongation of coagulation time and normal plasma (cross mixing test). That is, in the case of congenital coagulation disorder, prolongation of coagulation time is corrected by mixing with normal plasma, but in the case of acquired coagulation disorder, prolongation of coagulation time is not corrected.

Acquired coagulation disorders caused by autoantibodies are known to have different conditions depending on the type of autoantibody. For example, patients having autoantibodies to blood coagulation factors (also called as coagulation factor inhibitors) generally show bleeding symptoms. On the other hand, although autoantibodies called lupus anticoagulant (LA) inhibit phospholipids necessary for phospholipid-dependent coagulation reaction, patients having LA show thrombotic conditions. Therefore, it is clinically important to differentiate specimens containing coagulation factor inhibitors from specimens containing LA. However, as described above, since prolongation of coagulation time is observed in either specimen, it is difficult to differentiate them in a usual coagulation test.

Currently, in the cross mixing test, a method of measuring coagulation time for the sample immediately after preparation and the sample incubated at 37☐C for 2 hours, and differentiating the specimens containing coagulation factor inhibitors from the specimens containing LA, based on the pattern change in a graph obtained by plotting the coagulation time of each obtained sample and the mixing ratio of normal plasma and test plasma is performed. For example, Non Patent Literature 1 discloses that coagulation factor inhibitors and LA are differentiated, based on that the coagulation factor inhibitors are temperature and time dependent, and LA does not depend on them. However, differentiation by distinguishing the pattern change in a graph requires experience, and there are many cases where it is difficult to differentiate for one who is not a skilled person.

On the other hand, as for LA, a method of making a determination using an index for quantitatively evaluating the result of cross mixing test called ICA (Index of Circulating Anticoagulant) is known (see Non Patent Literature 2). ICA is calculated from the coagulation time of test plasma, normal plasma, and their equivalent mixtures. When the calculated ICA value is equal to or greater than a predetermined threshold value, it is determined that the test plasma contains LA. In addition, one of the present inventors has devised an index called RC-S (Response Curve-Score) and used it to detect LA-positive specimens (see Non Patent Literature 3).

CITATIONS LIST

Non Patent Literatures

Non Patent Literature 1: Collins P. et al., Consensus recommendations for the diagnosis and treatment of acquired hemophilia A. BMC Research Notes 2010; 3:161-169

Non Patent Literature 2: Pengo V. et al., Update of the guidelines for lupus anticoagulant detection. Journal of Thrombosis and Haemostasis 2009; 7:1737-1740

Non Patent Literature 3: Evaluation and usefulness of LA detection by new determination method of cross mixing test, The Official journal of Japanese Society of Laboratory Medicine, volume 60, compensation booklet, page 166, 2012

However, an index for quantitatively evaluating whether or not a blood specimen contains a coagulation factor inhibitor, based on the results of the cross mixing test, has not been known so far. Therefore, a means capable of simply determining whether the blood specimen is suspected of being a specimen containing a coagulation factor inhibitor, by newly finding such an index, is desired.

SUMMARY OF THE INVENTION

According to a first aspect of the present invention, there is provided a method of acquiring information on a cause of prolongation of coagulation time. This method includes a step of measuring first coagulation time which is coagulation time of a blood specimen of a subject, second coagulation time which is coagulation time of a normal blood specimen, and third coagulation time which is coagulation time of a mixed specimen obtained by mixing the blood specimen of a subject with the normal blood specimen, using a coagulation time measuring reagent, a step of measuring fourth coagulation time which is coagulation time of the blood specimen of a subject incubated under predetermined conditions, fifth coagulation time which is coagulation time of the normal blood specimen incubated under the predetermined conditions, and sixth coagulation time which is coagulation time of the mixed specimen incubated under the predetermined conditions, using the reagent, a step of acquiring a first quantification index based on the first, second and third coagulation times, and acquiring a second quantification index based on the fourth, fifth and sixth coagulation times, and a step of executing calculation using the value of the first quantification index and the value of the second quantification index, and acquiring a calculation result as the information on a cause of prolongation of coagulation time.

According to a second aspect of the present invention, a blood coagulation analyzer is provided. This analyzer comprises a measurement sample preparing unit for preparing a measurement sample obtained by admixing a specimen and a coagulation time measuring reagent, an optical information acquiring unit for irradiating the prepared measurement sample with light and acquiring optical information on the light amount from the measurement sample, a control unit, an input unit, and a display unit. This analyzer is characterized in that the control unit controls the measurement sample preparing unit so as to prepare a first measurement sample obtained by admixing a blood specimen of a subject and the reagent, a second measurement sample obtained by admixing a normal blood specimen and the reagent, and a third measurement sample obtained by admixing a mixed specimen in which the blood specimen of a subject and the normal blood specimen are mixed and the reagent, controls the optical information acquiring unit so as to acquire first, second and third optical information from the first, second and third measurement samples, respectively, acquires first, second and third coagulation times from the first, second and third optical information, respectively, acquires a value of a first quantification index from the first, second and third coagulation times, and when the input unit receives an input of a fourth coagulation time acquired from the blood specimen of a subject incubated under predetermined conditions, a fifth coagulation time acquired from the normal blood specimen incubated under the predetermined conditions, and a sixth coagulation time acquired from the mixed specimen incubated under the predetermined conditions, the control unit acquires a value of a second quantification index based on the fourth, fifth and sixth coagulation times, executes calculation using the value of the first quantification index and the value of the second quantification index, and outputs the calculation result to the display unit as the information on a cause of prolongation of coagulation time.

According to a third aspect of the present invention, there is provided a blood coagulation analyzer. This analyzer comprises a measurement sample preparing unit for preparing a measurement sample obtained by admixing a specimen and a coagulation time measuring reagent, an optical information acquiring unit for irradiating the prepared measurement sample with light and acquiring optical information on the light amount from the measurement sample, an incubation section for incubating the specimen under predetermined conditions, a control unit, and a display unit. This analyzer is characterized in that the control unit controls the incubation section so as to incubate a part of a blood specimen of a subject, a part of a normal blood specimen, and a part of a mixed specimen in which the blood specimen of a subject and the normal blood specimen are mixed under the predetermined conditions, controls the measurement sample preparing unit so as to prepare a first measurement sample in which the blood specimen of a subject and the reagent are admixed, a second measurement sample in which the normal blood specimen and the reagent are admixed, and a third measurement sample obtained by admixing the mixed specimen and the reagent, controls the optical information acquiring unit so as to acquire first, second and third optical information from the first, second and third measurement samples, respectively, controls the measurement sample preparing unit so as to prepare a fourth measurement sample in which a blood specimen of a subject incubated under the predetermined conditions and the reagent are admixed, a fifth measurement sample in which a normal blood specimen incubated under the predetermined conditions and the reagent are admixed, and a sixth measurement sample obtained by admixing the mixed specimen incubated under the predetermined conditions and the reagent, controls the optical information acquiring unit so as to acquire fourth, fifth and sixth optical information from the fourth, fifth and sixth measurement samples, respectively, acquires first, second and third coagulation times from the first, second and third optical information, respectively, acquires a value of a first quantification index from the first, second and third coagulation times, acquires fourth, fifth and sixth coagulation times from the fourth, fifth and sixth optical information, respectively, acquires a value of a second quantification index from the fourth, fifth and sixth coagulation times, executes calculation using the value of the first quantification index and the value of the second quantification index, and outputs the calculation result to the display unit as the information on a cause of prolongation of coagulation time.

A fourth aspect of the present invention provides a system for blood coagulation analysis, comprising a computer containing a processor and a memory under control of the processor. A computer program for making the computer execute the steps of acquiring a first optical information of a first measurement sample in which a blood specimen of a subject and a coagulation time measuring reagent are admixed, a second optical information of a second measurement sample in which a normal blood specimen and the reagent are admixed and a third optical information of a third measurement sample obtained by admixing a mixed sample in which a mixed specimen in which the blood specimen of a subject and the normal blood specimen are mixed and the reagent, acquiring a fourth optical information of a fourth measurement sample in which the blood specimen of a subject incubated under predetermined conditions and the reagent are admixed, a fifth optical information of a fifth measurement sample in which the normal blood specimen incubated under the predetermined conditions and the reagent are admixed and a sixth optical information of a sixth measurement sample obtained by admixing the mixed specimen incubated under the predetermined conditions and the reagent, acquiring first, second and third coagulation times from the first, second and third optical information, respectively, and acquiring fourth, fifth and sixth coagulation times from the fourth, fifth and sixth optical information, respectively, acquiring a value of a first quantification index from the first, second and third coagulation times and acquiring a value of a second quantification index from the fourth, fifth and sixth coagulation times, and executing calculation using the value of the first quantification index and the value of the second quantification index and acquiring the calculation result as the information on a cause of prolongation of coagulation time, is recorded in the memory.

A fifth aspect of the present invention provides a computer program for blood coagulation analysis, which is recorded on a computer readable medium. This computer program is characterized in making the computer execute the steps of acquiring a first optical information of a first measurement sample in which a blood specimen of a subject and a coagulation time measuring reagent are admixed, a second optical information of a second measurement sample in which a normal blood specimen and the reagent are admixed and a third optical information of a third measurement sample obtained by admixing a mixed sample in which a mixed specimen in which the blood specimen of a subject and the normal blood specimen are mixed and the reagent, acquiring a fourth optical information of a fourth measurement sample in which a blood specimen of a subject incubated under predetermined conditions and the reagent are admixed, a fifth optical information of a fifth measurement sample in which a normal blood specimen incubated under the predetermined conditions and the reagent are admixed and a sixth optical information of a sixth measurement sample obtained by admixing the mixed specimen incubated under the predetermined conditions and the reagent, acquiring first, second and third coagulation times from the first, second and third optical information, respectively, and acquiring fourth, fifth and sixth coagulation times from the fourth, fifth and sixth optical information, respectively, acquiring a value of a first quantification index from the first, second and third coagulation times and acquiring a value of a second quantification index from the fourth, fifth and sixth coagulation times, and executing calculation using the value of the first quantification index and the value of the second quantification index and acquiring the calculation result as the information on a cause of prolongation of coagulation time.

According to the present invention, it is possible to quantitatively evaluate whether a blood specimen of a subject has a cause of prolongation of coagulation time such as a coagulation factor inhibitor.

BRIEF DESCRIPTION OF THE DRAWINGS

FIG. 11B is a view showing an example of an input screen for delayed coagulation time.

DETAILED DESCRIPTION OF THE PREFERRED EMBODIMENTS

Figure 1:
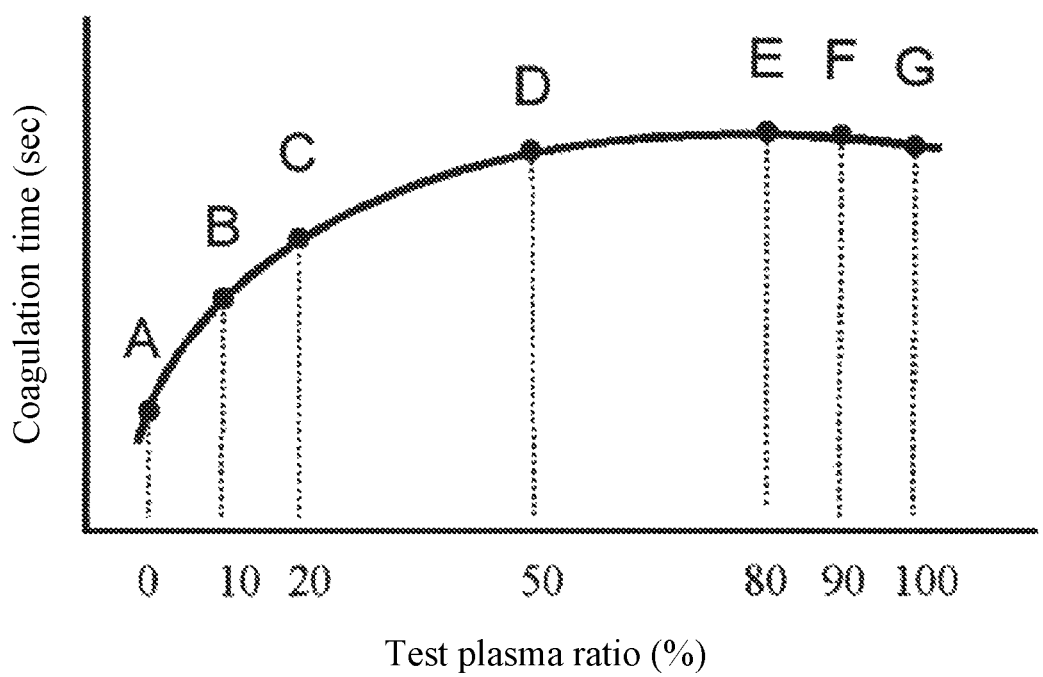
FIG. 1 is an example of a graph of a cross mixing test. In the figure, A shows coagulation time of normal plasma, B shows coagulation time of mixed plasma with a test plasma ratio of 10% (v/v), C shows coagulation time of mixed plasma with a test plasma ratio of 20% (v/v), D shows coagulation time of mixed plasma with a test plasma ratio of 50% (v/v), E shows coagulation time of mixed plasma with a test plasma ratio of 80% (v/v), F shows coagulation time of mixed plasma with a test plasma ratio of 90% (v/v), and G shows coagulation time of the test plasma.

[1. Method for Acquiring Information on Cause of Prolongation of Coagulation Time]

A method for acquiring information on a cause of prolongation of coagulation time according to the first aspect (hereinafter, also simply referred to as "method") will be described below. In the method according to the present embodiment, first, the coagulation time is measured for each of a blood specimen of a subject, a normal blood specimen, and a mixed specimen thereof. The coagulation time is also measured for each specimen incubated under predetermined conditions described later.

In the present embodiment, the blood specimen of a subject may be blood (whole blood) obtained from the subject or plasma prepared from the blood. Among them, plasma is preferable, and platelet-removed plasma is more preferable. The platelets can be removed by a known method such as centrifugation or filter separation.

In a preferred embodiment, the blood specimen of a subject is a blood specimen suspected of having a cause of prolongation of coagulation time. Examples of such a blood specimen include specimens in which prolongation of coagulation time has been observed by an ordinary coagulation test, specimen groups obtained from a plurality of subjects including a person suspected of having a cause of prolongation of coagulation time, and the like.

In the present embodiment, the cause of prolongation of coagulation time is not particularly limited, and examples thereof include a coagulation factor inhibitor, LA, a coagulation factor deficiency, a drug acting on blood coagulation, and the like. The coagulation factor inhibitor is not particularly limited, and examples thereof include a factor VIII inhibitor, a factor IX inhibitor, a factor V inhibitor, and the like. The coagulation factor suspected of having deficiency is not particularly limited, and examples thereof include factor V, factor VII, factor VIII, factor IX, factor X, factor XI, factor XII, and the like. The agent acting on blood coagulation is not particularly limited, and examples thereof include heparin, warfarin, and the like.

The normal blood specimen may be blood obtained from a healthy person or plasma prepared from the blood. Alternatively, commercially available normal plasma may be used. Examples of commercially available normal plasma include CRYOcheck Pooled Normal Plasma (Precision BioLogic Inc) and the like.

Since the method according to the present embodiment is based on the principle of cross mixing test, a specimen in which a blood specimen of a subject and a normal blood specimen are mixed at least one mixing ratio (hereinafter, also referred to as "mixed specimen") is used. The mixing ratio of the blood specimen of a subject and the normal blood specimen can be appropriately determined according to the amount of the blood specimen of a subject or the type of the quantification index described later. The ratio of the blood specimen of a subject in the mixed specimen is selected at least one from, for example, 5, 10, 15, 20, 25, 30, 35, 40, 45, 50, 55, 60, 65, 70, 75, 80, 85, 90, and 95% (v/v). Among them, it is preferable to prepare a mixed specimen in which the ratio of the blood specimen of a subject is 50% (v/v). Preparation of the mixed specimen may be carried out by a manual method or may be carried out by a fully automatic coagulation time measurement apparatus.

In the present embodiment, the coagulation time of a specimen not incubated under predetermined conditions and the coagulation time of a specimen incubated under the conditions are measured, thus, at least two sets each of the blood specimen of a subject, the normal blood specimen and the mixed specimen are prepared.

In the present embodiment, the first coagulation time is coagulation time obtained by measuring the blood specimen of a subject without incubating under predetermined conditions described later. The second coagulation time is coagulation time obtained by measuring the normal blood specimen without incubating under predetermined conditions described later. The third coagulation time is coagulation time obtained by measuring the mixed specimen without incubating under predetermined conditions described later. That is, the measurement of the first, second and third coagulation times is not different from measuring normal coagulation time for each of the above specimens. For example, the measurement of the first, second and third coagulation times can be performed by preparing each of the above specimens and then measuring coagulation time usually within less than 45 minutes, preferably within 30 minutes, and more preferably within 15 minutes. The first, second and third coagulation times are herein also called as "immediate coagulation time".

In the present embodiment, the fourth coagulation time is coagulation time obtained by measuring the blood specimen of a subject after incubating under predetermined conditions. The fifth coagulation time is coagulation time obtained by measuring the normal blood specimen after incubating under predetermined conditions. The sixth coagulation time is coagulation time obtained by measuring the mixed specimen after incubating under predetermined conditions. As the predetermined conditions, the temperature and time for promoting an inhibition reaction by the coagulation factor inhibitor may be set. Such conditions include, for example, incubation at 15° C. or more and 40° C. or less for 45 minutes or more and 4 hours or less, and preferably 1 hour or more and 3 hours or less. In this technique, conditions for incubating at 37° C. for 2 hours are widely used.

In the present embodiment, measurement of the fourth, fifth and sixth coagulation times are the same as the measurement of the first, second and third coagulation times, except that each of the above prepared specimens is incubated under predetermined conditions. For example, the measurement of the fourth, fifth and sixth coagulation times can be performed by preparing each of the above specimens, incubating them under predetermined conditions, and then measuring coagulation time usually within less than 45 minutes, preferably within 30 minutes, and more preferably within 15 minutes. The means for incubating a specimen is not particularly limited. When incubation is performed by a manual method, examples of the means include incubation of a specimen in a water bath or thermostat set at a predetermined temperature. Alternatively, it may be performed by a fully automatic coagulation time measurement apparatus having a function of incubating a specimen for a certain period of time. The fourth, fifth and sixth coagulation times are herein also called as "delayed coagulation time".

In the present embodiment, the coagulation time measuring reagent (hereinafter, also simply referred to as "reagent") may be a reagent for measuring coagulation time based on the measurement principle known in the art. Examples thereof include reagents for measuring at least one of prothrombin time (PT), activated partial thromboplastin time (APTT), dilute prothrombin time (dPT), dilute activated partial thromboplastin time (dAPTT), kaolin clotting time (KCT), dilute Russell viper venom clotting time (dRVVT), thrombin time (TT), and dilute thrombin time (dTT). Among these, the dAPTT measuring reagent is preferable. Also, commercially available coagulation time measuring reagents and reagent kits may be used. For example, as the APTT measuring reagent, Thrombocheck APTT-SLA (Sysmex Corporation), Thrombocheck APTT (Sysmex Corporation), Actin FSL (Sysmex Corporation) and the like are known.

The measurement of each coagulation time is performed on a measurement sample obtained by admixing each of the above specimens and the coagulation time measuring reagent. Preparation of the measurement sample itself is known in the art. For example, the reaction time between each specimen and the reagent is usually 1 minute or more and 10 minutes or less, and preferably 3 minutes or more to 5 minutes or less. The temperature condition is usually 25° C. or more and 45° C. or less, and preferably 35° C. or more and 38° C. or less. Preparation of the measurement sample may be carried out by a manual method or may be carried out by a fully automatic coagulation time measurement apparatus, and is preferably carried out by a fully automatic coagulation time measurement apparatus. Examples of the fully automatic coagulation time measurement apparatus include CS-5100 (Sysmex Corporation), CS-2400 (Sysmex Corporation), and CS-2000i (Sysmex Corporation).

The procedure for measuring coagulation time of the measurement sample itself is known in the art. Measurement of coagulation time of the measurement sample may be carried out by a manual method or may be carried out by a fully automatic coagulation time measurement apparatus Preferably, measurement is carried out by a fully automatic coagulation time measurement apparatus. When the coagulation time is measured by this apparatus, the measurement sample is irradiated with light, and the coagulation time is calculated based on the obtained optical information. The light to be irradiated may be light which is usually used for measuring coagulation time, and is for example, light having a wavelength of around 660 nm. A light source is not particularly limited, and examples thereof include a light emitting diode, a halogen lamp, and the like. By irradiating the measurement sample with light from the light source, scattered light and transmitted light are generated from the measurement sample. In the present embodiment, examples of the optical information on the light amount include the amount of scattered light or the amount of transmitted, and scattered light intensity, transmittance, absorbance and the like are preferable.

In the present embodiment, which of the immediate coagulation time or the delayed coagulation time is measured first is not particularly limited. Because measurement of delayed coagulation time requires incubation time, the immediate coagulation time may be measured first in the meantime.

In the present embodiment, the immediate coagulation time and the delayed coagulation time may be measured by the same means or may be measured by different means. When measured by different means, for example, the immediate coagulation time may be measured with a fully automatic coagulation time measurement apparatus, and the delayed coagulation time may be measured by a manual method. Alternatively, the immediate coagulation time may be measured by a manual method, and the delayed coagulation time may be measured with a fully automatic coagulation time measurement apparatus. Also, in the case where both the immediate coagulation time and the delayed coagulation time are measured with a fully automatic coagulation time measurement apparatus, the apparatus may be the same apparatus or a different apparatus.

Next, in the method according to the present embodiment, the first quantification index is acquired based on the first, second, and third coagulation times, and the second quantification index is acquired based on the fourth, fifth, and sixth coagulation times.

In the present embodiment, the quantification index is not particularly limited as long as it is an index for quantitatively evaluating the result of cross mixing test, based on the coagulation time of a blood specimen of a subject, a normal blood specimen and/or a mixed specimen thereof. In addition, a well-known quantification index may be used. Examples of known quantification indexes include ICA, PC (Percent Correction), RC-S, and the like. Here, ICA is disclosed in Non Patent Document 2, PC is disclosed in Chang S-H. et al., "Percent Correction" Formula for Evaluation of Mixing Studies, Am J Clin Pathol 2002; 117:62-73, and RC-S is disclosed in Non Patent Document 3. Hereinafter, ICA, PC and RC-S will be described with reference to FIG. 1. A to G in each of the following formulae correspond to A to G in FIG. 1, respectively.

ICA is also called as Rosner Index, and is an index used to determine LA specimens. ICA is calculated by the following formula.

$$ICA = [(D-A)/G] \times 100$$

(in the formula, A: coagulation time of normal plasma, D: coagulation time of mixed plasma with a test plasma ratio of 50% (v/v), G: coagulation time of test plasma)

The calculation formula of PC differs according to the test plasma ratio in the mixed specimen, as described below.

$$PC(9:1) = [(G-B)/(G-A)] \times 100$$

$$PC(8:2) = [(G-C)/(G-A)] \times 100$$

$$PC(5:5) = [(G-D)/(G-A)] \times 100$$

$$PC(2:8) = [(G-E)/(G-A)] \times 100$$

$$PC(1:9) = [(G-F)/(G-A)] \times 100$$

(in the formula, A: coagulation time of normal plasma, B: coagulation time of mixed plasma with a test plasma ratio of 10% (v/v), C: coagulation time of mixed plasma with a test plasma ratio of 20% (v/v), D: coagulation time of mixed plasma with a test plasma ratio of 50% (v/v), E: coagulation time of mixed plasma with a test plasma ratio of 80% (v/v), F: coagulation time of mixed plasma with a test plasma ratio of 90% (v/v), G: coagulation time of test plasma)

RC-S is an index applying Rosner index, and is calculated as follows. First, the scores for mixed specimens with test plasma ratios of 20% and 50% (v/v) are calculated by the following formula.

$$RC\text{-}S(20) = [(C-B)/D] \times 100$$

$$RC\text{-}S(50) = [(D-C)/E] \times 100$$

(in the formula, B: coagulation time of mixed plasma with a test plasma ratio of 10% (v/v), C: coagulation time of mixed plasma with a test plasma ratio of 20% (v/v), D: coagulation time of mixed plasma with a test plasma ratio of 50% (v/v), E: coagulation time of mixed plasma with a test plasma ratio of 80% (v/v))

Next, for the mixed specimens with test plasma ratios of 20% and 50% (v/v), a control score in the case where the reaction curve in FIG. 1 is assumed to be straight line is calculated by the following formula.

$$RC\text{-}Sc(20) = [[(3 \times B + D)/4 - B]/D] \times 100$$

$$RC\text{-}Sc(50) = [[(C+E)/2 - B]/E] \times 100$$

(in the formula, B: coagulation time of mixed plasma with a test plasma ratio of 10% (v/v), C: coagulation time of mixed plasma with a test plasma ratio of 20% (v/v), D: coagulation time of mixed plasma with a test plasma ratio of 50% (v/v), E: coagulation time of mixed plasma with a test plasma ratio of 80% (v/v))

Then, the ratio of score (S) to control score (Sc) is calculated for each of the mixed specimens with test plasma ratios of 20% and 50% (v/v), and the sum of the two calculated ratios is used as a quantification index (see the following formula).

$$S/Sc(20+50) = (RC\text{-}S(20)/RC\text{-}Sc(20)) \times 100 + (RC\text{-}S(50)/RC\text{-}Sc(50)) \times 100$$

In the present embodiment, the types of the first quantification index and the second quantification index may be the same or different, but are preferably the same.

Moreover, in the method according to the present embodiment, calculation is executed using the value of the first quantification index and the value of the second quantification index obtained above, and the calculation result is acquired as the information on a cause of prolongation of coagulation time.

In the present embodiment, the above calculation is not particularly limited, but it is preferred to calculate the value of ratio or difference between the value of the first quantification index and the value of the second quantification index, or the value by combining the value of ratio and the value of difference. Incidentally, examples of the value by combining the value of ratio and the value of difference include the sum, difference, product, and ratio of the value of ratio and the value of difference, and the like.

In the present embodiment, the value of ratio may be a value calculated by one of the following formulae.

(Value of ratio)=(Value of first quantification index)/(Value of second quantification index)

or (Value of ratio)=(Value of second quantification index)/(Value of first quantification index)

In the present embodiment, the ratio (%) obtained by multiplying the value calculated from the above formula by 100 may be acquired as the value of ratio. Alternatively, the value obtained by adding a constant to the value calculated from the above formula may be acquired as the value of ratio.

In the present embodiment, the value of difference may be a value calculated by one of the following formulae.

(Value of difference)=(Value of first quantification index)−(Value of second quantification index)

or (Value of difference)=(Value of second quantification index)−(Value of first quantification index)

In the present embodiment, the value obtained by multiplying the value calculated from the above formula by a constant may be acquired as the value of difference.

The present inventors have found that the values of ratio and difference based on the immediate coagulation time and the delayed coagulation time enables differentiation between the coagulation factor inhibitor and other causes of prolongation. Therefore, in the method according to the present embodiment, the above calculation result can be acquired as the information on a cause of prolongation of coagulation time.

In the method according to the present embodiment, the information on a coagulation factor inhibitor in a blood specimen of a subject can be further acquired, based on the obtained information on a cause of prolongation of coagulation time. Specifically, the value of ratio or difference or the value by combining them is compared with the first threshold value, and based on the comparison result, the information on whether a blood specimen of a subject is suspected of being a specimen containing a coagulation factor inhibitor or suspected of being a specimen having a cause of prolongation other than the coagulation factor inhibitor is acquired.

For example, when the value of ratio is a value obtained by dividing the value of the second quantification index by the value of the first quantification index, the above information may be acquired as follows. That is, when the value of ratio is equal to or greater than the first threshold value, the information that the blood specimen of a subject is suspected of being a specimen containing a coagulation factor inhibitor can be acquired. Conversely, when the value of ratio is less than the first threshold value, the information that the blood specimen of a subject is suspected of being a specimen having a cause of prolongation other than the coagulation factor inhibitor can be acquired.

When the value of ratio is a value obtained by dividing the value of the first quantification index by the value of the second quantification index, the above information may be acquired as follows. That is, when the value of ratio is less than the first threshold value, the information that the blood specimen of a subject is suspected of being a specimen containing a coagulation factor inhibitor can be acquired. Conversely, when the value of ratio is equal to or greater than the first threshold value, the information that the blood specimen of a subject is suspected of being a specimen having a cause of prolongation other than the coagulation factor inhibitor can be acquired.

When the value of difference is a value obtained by subtracting the value of the first quantification index from the value of the second quantification index, the above information may be acquired as follows. That is, when the value of difference is equal to or greater than the first threshold value, the information that the blood specimen of a subject is suspected of being a specimen containing a coagulation factor inhibitor can be acquired. Conversely, when the value of difference is less than the first threshold value, the information that the blood specimen of a subject is suspected of being a specimen having a cause of prolongation other than the coagulation factor inhibitor can be acquired.

When the value of difference is a value obtained by subtracting the value of the second quantification index from the value of the first quantification index, the above information may be acquired as follows. That is, when the value of difference is less than the first threshold value, the information that the blood specimen of a subject is suspected of being a specimen containing a coagulation factor inhibitor can be acquired. Conversely, when the value of difference is equal to or greater than the first threshold value, the information that the blood specimen of a subject is suspected of being a specimen having a cause of prolongation other than the coagulation factor inhibitor can be acquired.

In the present embodiment, the first threshold value is not particularly limited. For example, by accumulating data on coagulation factor inhibitor-positive specimens and specimens having other cause of prolongation such as LA, a first threshold value corresponding to the value of ratio or difference or the value by combining them can be empirically set. Alternatively, the immediate coagulation time and the delayed coagulation time are measured for each of a coagulation factor inhibitor-positive specimen group and a specimen group having other cause of prolongation such as LA, the value of ratio and/or difference between the value of the first quantification index and the value of the second quantification index is acquired, and a value that can clearly distinguish both groups can be set as the first threshold value, based on the acquired value of ratio and/or difference. For the calculation of the first threshold value, a statistical method such as ROC analysis may be used.

In the method according to the present embodiment, when acquiring the information that the blood specimen of a subject is suspected of being a specimen having a cause of prolongation other than the coagulation factor inhibitor, the information on LA in the blood specimen of a subject can be also acquired, based on the value of the first quantification index or the second quantification index.

Specifically, the value of the first quantification index or the second quantification index is compared with a second threshold value, and based on the comparison result, the information on whether the blood specimen of a subject is suspected of being a specimen containing LA or suspected of being a specimen having a cause of prolongation other than the coagulation factor inhibitor and LA can be acquired. That is, when any one value selected from the first quantification index and the second quantification index is equal to or greater than the second threshold value, the information that the blood specimen of a subject is suspected of being a specimen containing LA can be acquired. Conversely, when the value of the selected quantification index is less than the second threshold value, the information that the blood specimen of a subject is suspected of being a specimen having a cause of prolongation other than the coagulation factor inhibitor and LA can be acquired.

In the present embodiment, the second threshold value is not particularly limited. For example, by accumulating data on LA-positive specimens and specimens having other cause of prolongation, a second threshold value corresponding to the value of the first quantification index or the second quantification index can be empirically set. Alternatively, the immediate coagulation time and the delayed coagulation time are measured for each of an LA-positive specimen group and a specimen group having a cause of prolongation other than the coagulation factor inhibitor and LA, the value of the first quantification index and the value of the second quantification index are acquired, and a value that can clearly distinguish both groups can be set as the second threshold value based on the acquired values. For the calculation of the second threshold value, a statistical method such as ROC analysis may be used.

[2. Device, System and Computer Program for Analysis of Blood Coagulation]

Figure 2:
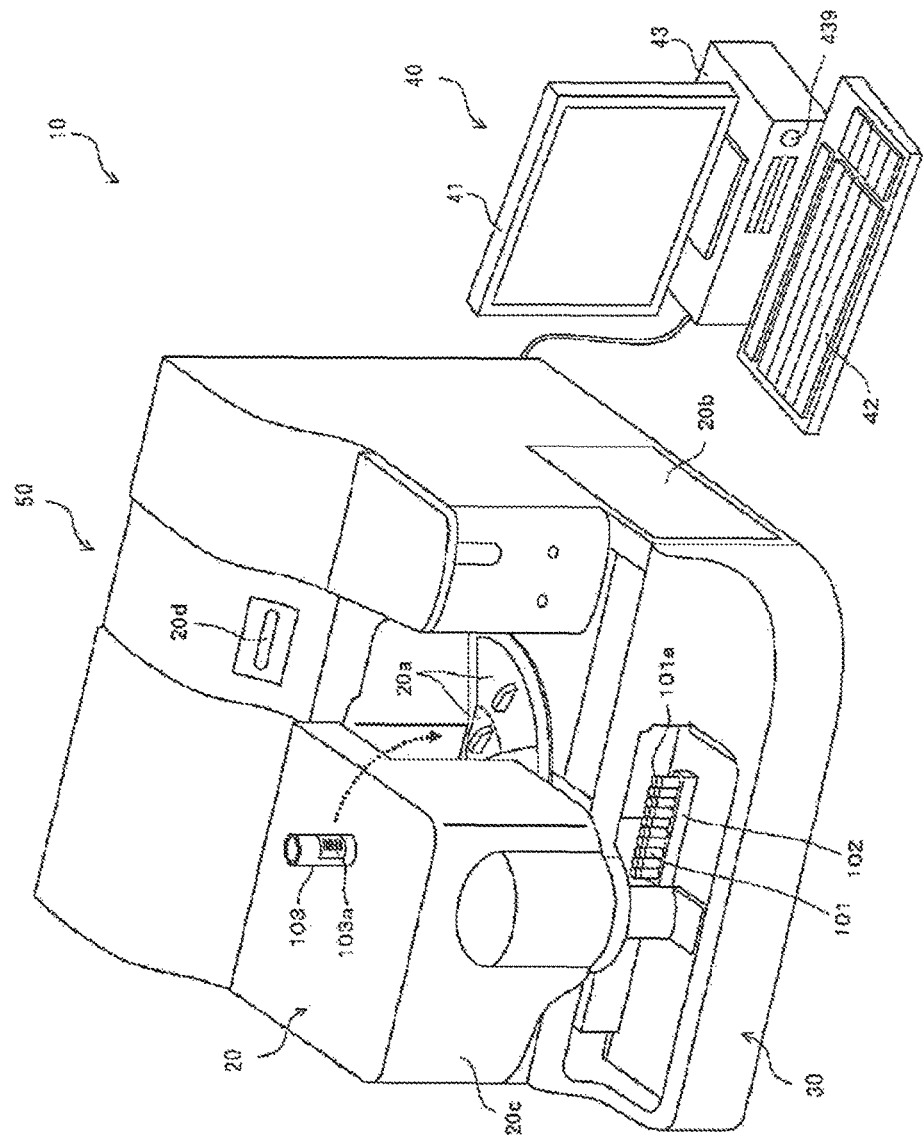
FIG. 2 is a perspective view showing an appearance configuration of a blood coagulation analyzer.

An example of the blood coagulation analyzer according to the present embodiment will be described below, with reference to the drawings. However, the present embodiment is not limited to this example. As shown in FIG. 2, a blood coagulation analyzer 10 includes a measurement device 50 for preparing and optically measuring a measurement sample, a control device 40 for analyzing measurement data acquired by the measurement device 50 and providing an instruction to the measurement device 50. The measurement device 50 includes a measurement unit 20 for acquiring optical information on the light amount from the measurement sample, and a specimen transporting section 30 arranged in front of the measurement unit 20.

The measurement unit 20 is provided with lids 20a and 20b, a cover 20c, and a power button 20d. A user can open the lid 20a and replace a reagent container 103 placed in reagent tables 11 and 12 (see FIG. 3) with a new reagent container 103, or a user can newly add another reagent container 103. To the reagent container 103 is attached a barcode label 103a printed with a barcode including the kind of the reagent to be accommodated and a reagent ID made up of serial number provided to the reagent.

Figure 3:
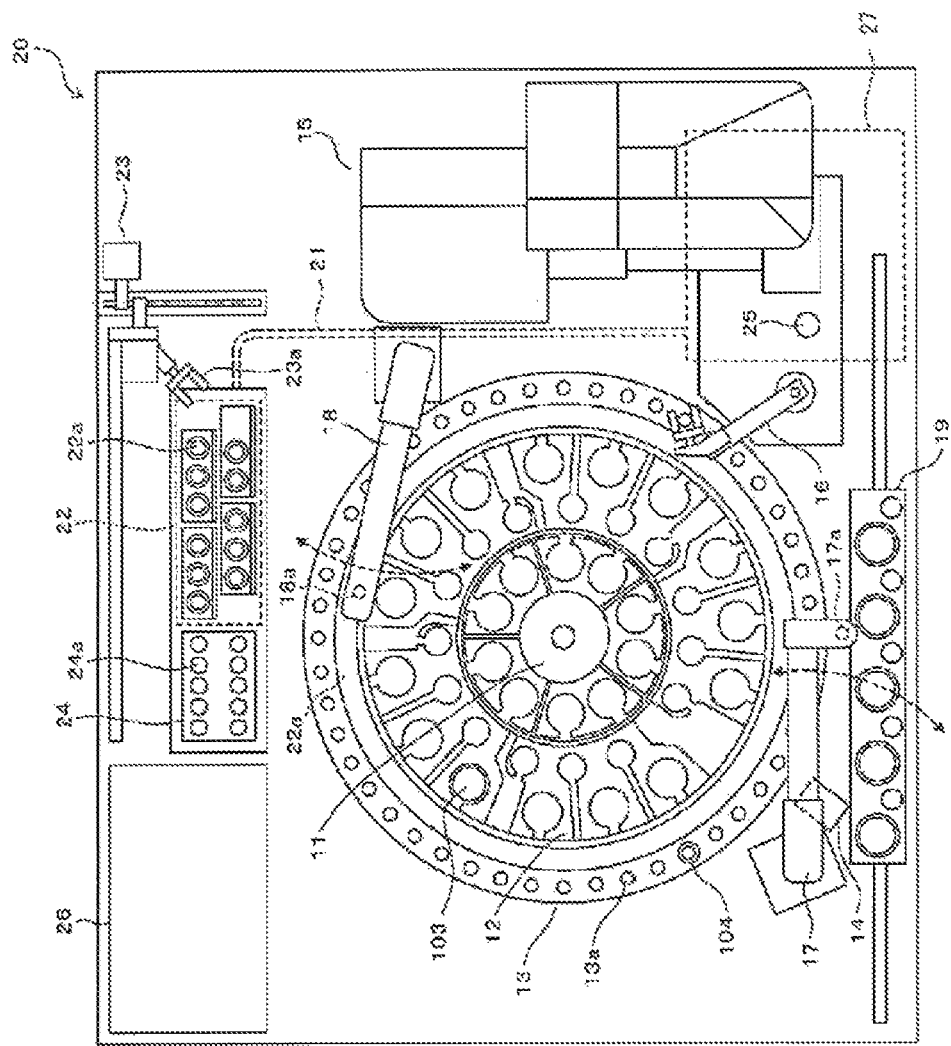
FIG. 3 is a plan view of the interior of a measurement device provided in the blood coagulation analyzer when viewed from above.

The user can open the lid 20b and replace a lamp unit 27 (see FIG. 3). The user can also open the cover 20c and replace a piercer 17a (see FIG. 3). The specimen transporting section 30 transports a specimen container 101 supported by a specimen rack 102 to an aspiration position by the piercer 17a. The specimen container 101 is hermetically sealed by a rubber lid 101a.

When using the blood coagulation analyzer 10, the user first presses the power button 20d of the measurement unit 20 to activate the measurement unit 20, and the user presses a power button 439 of the control device 40 to activate the control device 40. When the control device 40 is activated, a log-on screen is displayed on a display unit 41. The user inputs the user name and the password on the log-on screen to log on to the control device 40, and the user starts using the blood specimen analyzer 10.

The configuration of the measurement device will be described below. As shown in FIG. 3, the measurement unit 20 includes reagent tables 11 and 12, a cuvette table 13, a barcode reader 14, a cuvette supply section 15, a catcher 16, a specimen dispensing arm 17, a reagent dispensing arm 18, an urgent specimen setting section 19, an optical fiber 21, a detecting section 22, a cuvette transfer section 23, a warming section 24, a disposal port 25, a fluid section 26, and a lamp unit 27.

(Measurement Sample Preparing Unit)

Each of the reagent tables 11 and 12 and the cuvette table 13 has an annular shape. Each of the reagent tables 11 and 12 and the cuvette table 13 is configured rotatably. Each of the reagent tables 11 and 12 corresponds to a reagent storing section, onto which a reagent container 103 is placed. The barcode of the reagent container 103 placed on the reagent tables 11 and 12 is read by the barcode reader 14. Information (kind of reagent, reagent ID) read from the barcode is input to the control device 40 and stored in a hard disk 434 (see FIG. 8). Also, a reagent container 103 accommodating a normal blood specimen for preparation of a mixed specimen may be placed on the reagent tables 11 and/or 12.

The cuvette table 13 is formed with a support portion 13a composed of a plurality of holes capable of supporting a cuvette 104. A new cuvette 104 introduced into the cuvette supply section 15 by the user is sequentially transferred by the cuvette supply section 15, and the cuvette 104 is placed on the support portion 13a of the cuvette table 13 by the catcher 16.

A stepping motor is connected to each of the specimen dispensing arm 17 and the reagent dispensing arm 18 so as to be able to move up and down and rotatably. A piercer 17a of which a tip is sharply formed is provided at the tip of the specimen dispensing arm 17, so that the lid 101a of the specimen container 101 can be punctured. A pipette 18a is provided at the tip of the reagent dispensing arm 18. The tip of the pipette 18a is formed flat unlike the piercer 17a. An electrostatic capacitance type liquid level detection sensor 213 (see FIGS. 4A and 4B) is connected to the pipette 18a.

When the specimen container 101 is transported to a predetermined position by the specimen transporting section 30 (see FIG. 2), the piercer 17a is positioned just above the specimen container 101 by the rotational movement of the specimen dispensing arm 17. Then, the specimen dispensing arm 17 is moved downward, the piercer 17a penetrates the lid 101a of the specimen container 101, and the blood specimen accommodated in the specimen container 101 is aspirated by the piercer 17a. When an urgent blood specimen is set in the urgent specimen setting section 19, the piercer 17a intervenes in the specimen supplied from the specimen transporting section 30 and aspirates the urgent blood specimen. The blood specimen aspirated by the piercer 17a is discharged into an empty cuvette 104 on the cuvette table 13.

The cuvette 104 into which the blood specimen has been discharged is transferred from the support portion 13a of the cuvette table 13 to a support portion 24a of the warming section 24 by a catcher 23a of the cuvette transfer section 23. The warming section 24 warms the blood specimen accommodated in the cuvette 104 placed in the support portion 24a at a predetermined temperature (for example, 37° C.) for a certain period of time. When the warming of the blood specimen by the warming section 24 is finished, the cuvette 104 is again gripped by the catcher 23a. Then, the cuvette 104 is positioned at a predetermined position while being gripped by the catcher 23a, and in this state, the reagent aspirated by the pipette 18a is discharged into the cuvette 104.

In the dispensing of the reagent by the pipette 18a, first, the reagent tables 11 and 12 are rotated, and the reagent container 103 that accommodates the reagent corresponding to the measurement item is transported to an aspiration position by the pipette 18a. Then, after the position of the pipette 18a in the vertical direction is positioned at the origin position, the pipette 18a is lowered until the lower end of the pipette 18a comes into contact with the liquid level of the reagent by the liquid level detection sensor 213. When the lower end of the pipette 18*a* comes into contact with the liquid level of the reagent, the pipette 18*a* is further lowered to an extent that a necessary amount of the reagent can be aspirated. Then, the lowering of the pipette 18*a* is stopped, and the reagent is aspirated by the pipette 18*a*. The reagent aspirated by the pipette 18*a* is discharged into the cuvette 104 gripped by the catcher 23*a*. Then, the blood specimen and the reagent in the cuvette 104 are agitated by the vibrating function of the catcher 23*a*. Thus, the measurement sample is prepared. Thereafter, the cuvette 104 that accommodates the measurement sample is transferred to a support portion 22*a* of the detecting section 22 by the catcher 23*a*.

(Optical Information Acquiring Unit)

Figure 5:
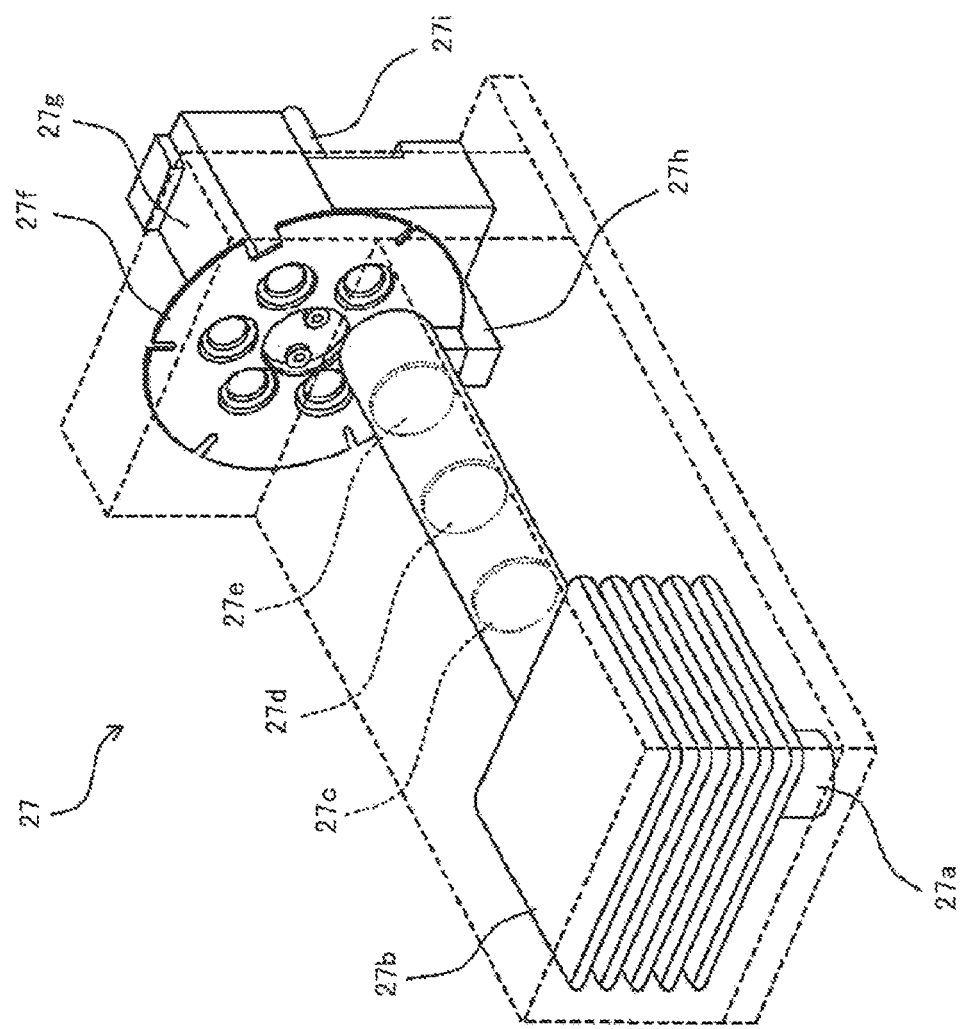
FIG. 5 is a diagram showing a configuration of a lamp unit provided in the measurement device.

The lamp unit 27 supplies light having plural kinds of wavelengths used for detection of an optical signal by the detecting section 22. An example of the configuration of the lamp unit 27 will be described with reference to FIG. 5. The lamp unit 27 corresponds to a light source. The lamp unit 27 includes a halogen lamp 27*a*, a lamp case 27*b*, condenser lenses 27*c* to 27*e*, a disk-shaped filter section 27*f*, a motor 27*g*, a light transmission type sensor 27*h*, and an optical fiber coupler 271.

Light from the lamp unit 27 is supplied to the detecting section 22 via the optical fiber 21. A plurality of hole-shaped support portions 22*a* are provided in the detecting section 22, and a cuvette 104 can be inserted into each of the support portions 22*a*. The end part of the optical fiber 21 is attached to each of the support portions 22*a*, and the cuvette 104 supported by the support portion 22*a* can be irradiated with light from the optical fiber 21. The detecting section 22 irradiates the cuvette 104 with light supplied from the lamp unit 27 via the optical fiber 21. The detecting section 22 detects the light amount of light to be transmitted through the cuvette 104 (or scattered light from the cuvette 104).

Figure 6A:
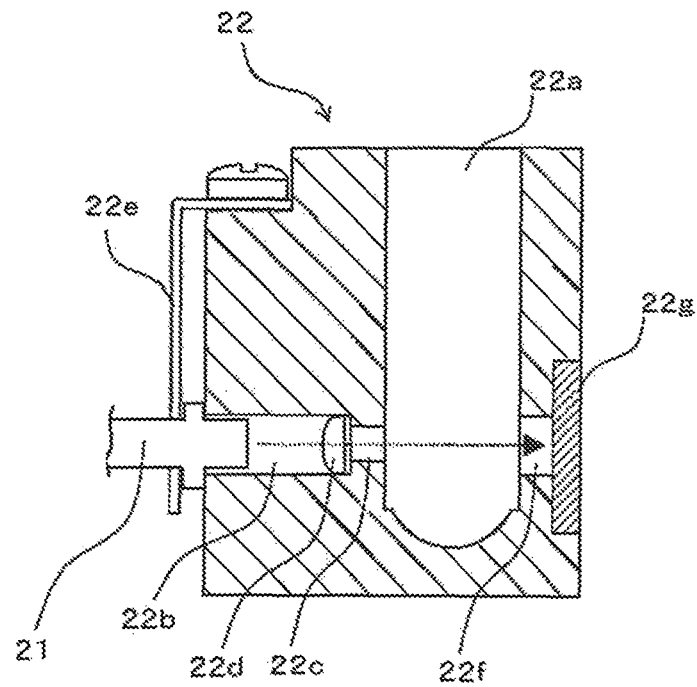
FIG. 6A is a diagram showing a configuration of a detection unit provided in the measurement device.

FIGS. 6A to 6D show an example of one configuration of the plurality of support portions 22*a* arranged in the detecting section 22, and the other support portions 22*a* have the same configuration. FIG. 6A, the detecting section 22 is formed with a circular hole 22*b* into which the tip of the optical fiber 21 is inserted. The detecting section 22 is further formed with a circular communication hole 22*c* for communicating the hole 22*b* with the support portion 22*a*. The diameter of the hole 22*b* is larger than the diameter of the communication hole 22*c*. A lens 22*d* for condensing light from the optical fiber 21 is arranged at the end of the hole 22*b*. Further, on the inner wall surface of the support portion 22*a*, a hole 22*f* is formed at a position facing the communication hole 22*c*. A photodetector 22*g* is arranged at the back of the hole 22*f*. The photodetector 22*g* corresponds to a light receiving portion. The photodetector 22*g* outputs an electric signal corresponding to the amount of received light. The light transmitted through the lens 22*d* is condensed on the light receiving surface of the photodetector 22*g*, through the communication hole 22*c*, the support portion 22*a*, and the hole 22*f*. The optical fiber 21 is prevented from falling off by a plate spring 22*e* in a state in which the end part of the optical fiber 21 is inserted into the hole 22*b*.

Figure 6B:
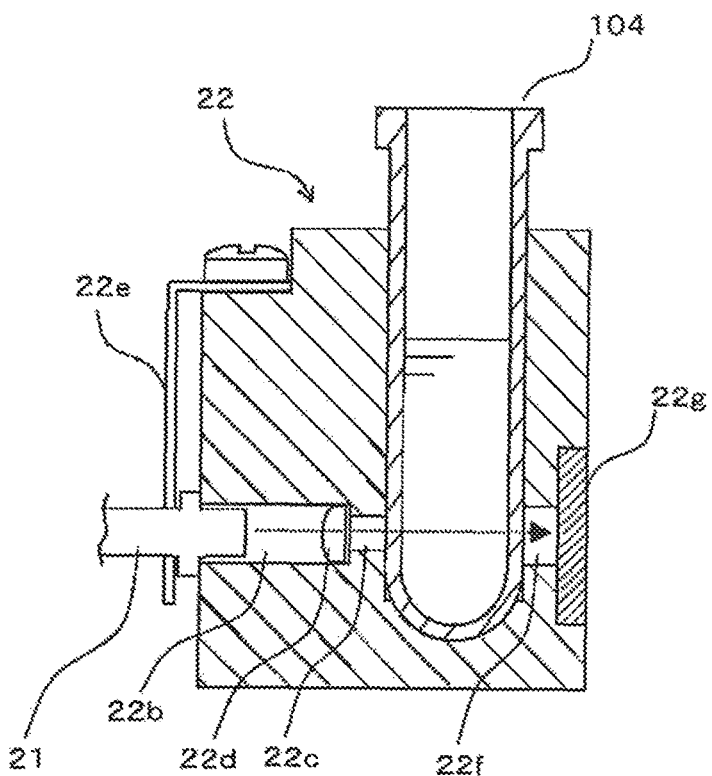
FIG. 6B is a diagram showing a configuration of a detection unit provided in the measurement device.

With reference to FIG. 6B, when the cuvette 104 is supported by the support portion 22*a*, the light condensed by the lens 22*d* is transmitted through the cuvette 104 and the sample accommodated in the cuvette 104, and the transmitted light enters the photodetector 22*g*. As the blood coagulation reaction progresses in the sample, the turbidity of the sample increases. Along with this, the amount of light to be transmitted through the sample (the amount of transmitted light) decreases, and the level of the detection signal of the photodetector 22*g* decreases.

Figure 6C:
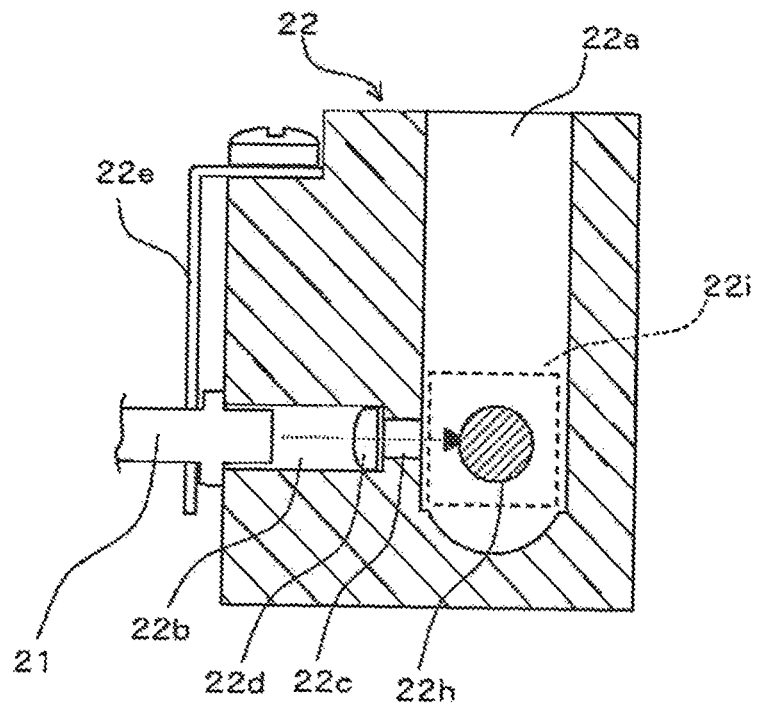
FIG. 6C is a diagram showing a configuration of a detection unit provided in the measurement device.
Figure 6D:
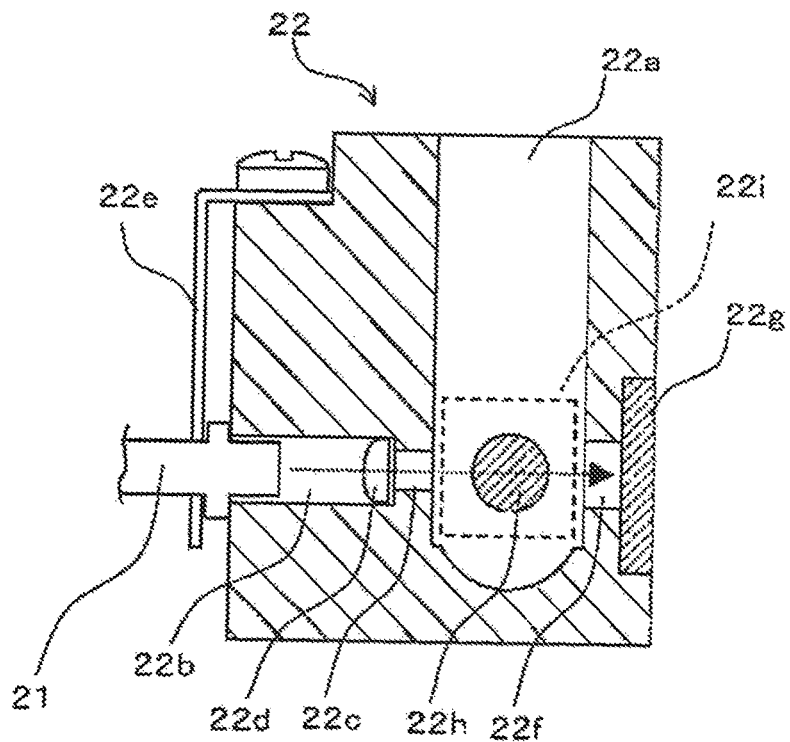
FIG. 6D is a diagram showing a configuration of a detection unit provided in the measurement device.

With reference to FIG. 6C, the configuration of the detecting section 22 when scattered light is used will be described. On the inner side surface of the support portion 22*a*, a hole 22*h* is provided at a position which is the same height as the communication hole 22*c*. A photodetector 22*i* is arranged at the back of the hole 22*h*. When the cuvette 104 is inserted into the support portion 22*a* and light is emitted from the optical fiber 21, the light scattered by the measurement sample in the cuvette 104 is irradiated to the photodetector 22*i* via the hole 22*h*. In this example, the detection signal from the photodetector 22*i* indicates the intensity of scattered light by the measurement sample. Also, as shown in FIG. 6D, both the light to be transmitted through the measurement sample and the light to be scattered by the measurement sample may be detected.

As described above, the detecting section 22 irradiates the cuvette 104 with light supplied from the lamp unit 27. The detecting section 22 acquires optical information from the measurement sample. The acquired optical information is transmitted to the control device 40. The control device 40 performs analysis based on the optical information. The control device 40 displays the analysis result on a display unit 41.

After completion of the measurement, the cuvette 104 that has become unnecessary is transported by the cuvette table 13. The transported cuvette 104 is discarded to the disposal port 25 by the catcher 16. During the measurement operation, the piercer 17*a* and the pipette 18*a* are appropriately washed with a liquid such as a cleaning liquid supplied from the fluid section 26.

Figure 4A:
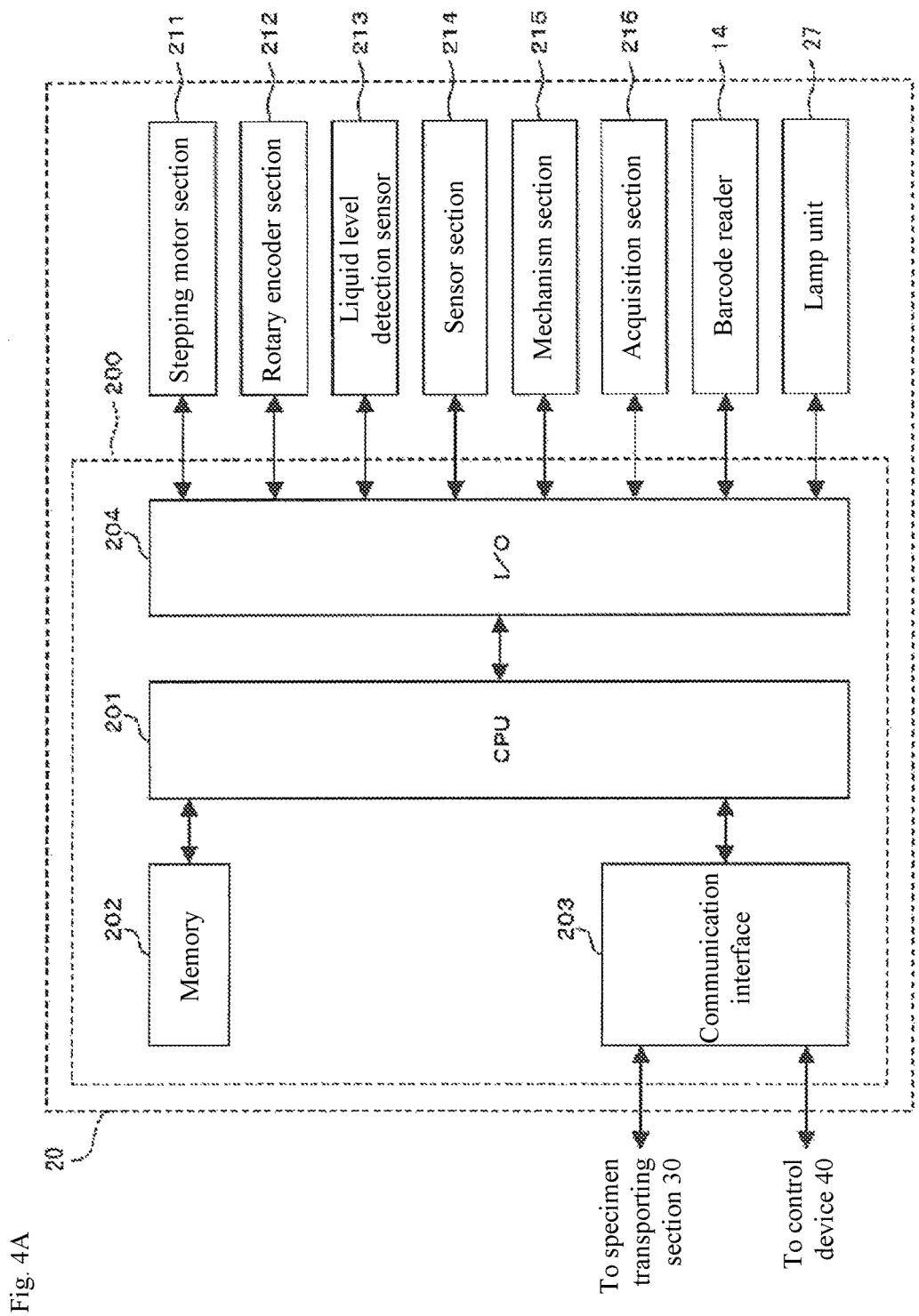
FIG. 4A is a diagram showing a configuration of a measurement device provided in the blood coagulation analyzer according to the second aspect.

The hardware configuration of the measurement device will be described below. As shown in FIG. 4A the measurement unit 20 includes a control section 200, a stepping motor section 211, a rotary encoder section 212, a liquid level detection sensor 213, a sensor section 214, a mechanism section 215, an acquisition section 216, a barcode reader 14, and a lamp unit 27.

The control section 200 includes a CPU 201, a memory 202, a communication interface 203, and an I/O interface 204. The CPU 201 executes a computer program stored in the memory 202. The memory 202 is composed of a ROM, a RAM, a hard disk, and the like. The CPU 201 drives the specimen transporting section 30 via the communication interface 203. The CPU 201 also transmits and receives instruction signals and data with the control device 40. The CPU 201 controls each section in the measurement unit 20 via the I/O interface 204. The CPU 201 also receives signals output from each section.

The stepping motor section 211 includes stepping motors for driving the reagent tables 11 and 12, the cuvette table 13, the catcher 16, the specimen dispensing arm 17, the reagent dispensing arm 18, and the cuvette transfer section 23, respectively. The rotary encoder section 212 includes a rotary encoder that outputs a pulse signal corresponding to the amount of rotational displacement of each stepping motor included in the stepping motor unit 211.

The liquid level detection sensor 213 is connected to the pipette 18*a* provided at the tip of the reagent dispensing arm 18. The liquid level detection sensor 213 detects that the lower end of the pipette 18*a* has come into contact with the liquid level of the reagent. The sensor section 214 includes a sensor for detecting that the vertical position of the pipette 18*a* is positioned at the origin position and a sensor for detecting that the power button 20*d* is pressed. The mechanism section 215 includes a mechanism for driving the cuvette supply section 15, the urgent specimen setting section 19, the warming section 24 and the fluid section 26, and an air pressure source which supplies pressure to the piercer 17a and the pipette 18a so that dispensing operation by the piercer 17a and the pipette 18a can be performed.

The acquisition section 216 includes a detection unit 22.

Figure 4B:
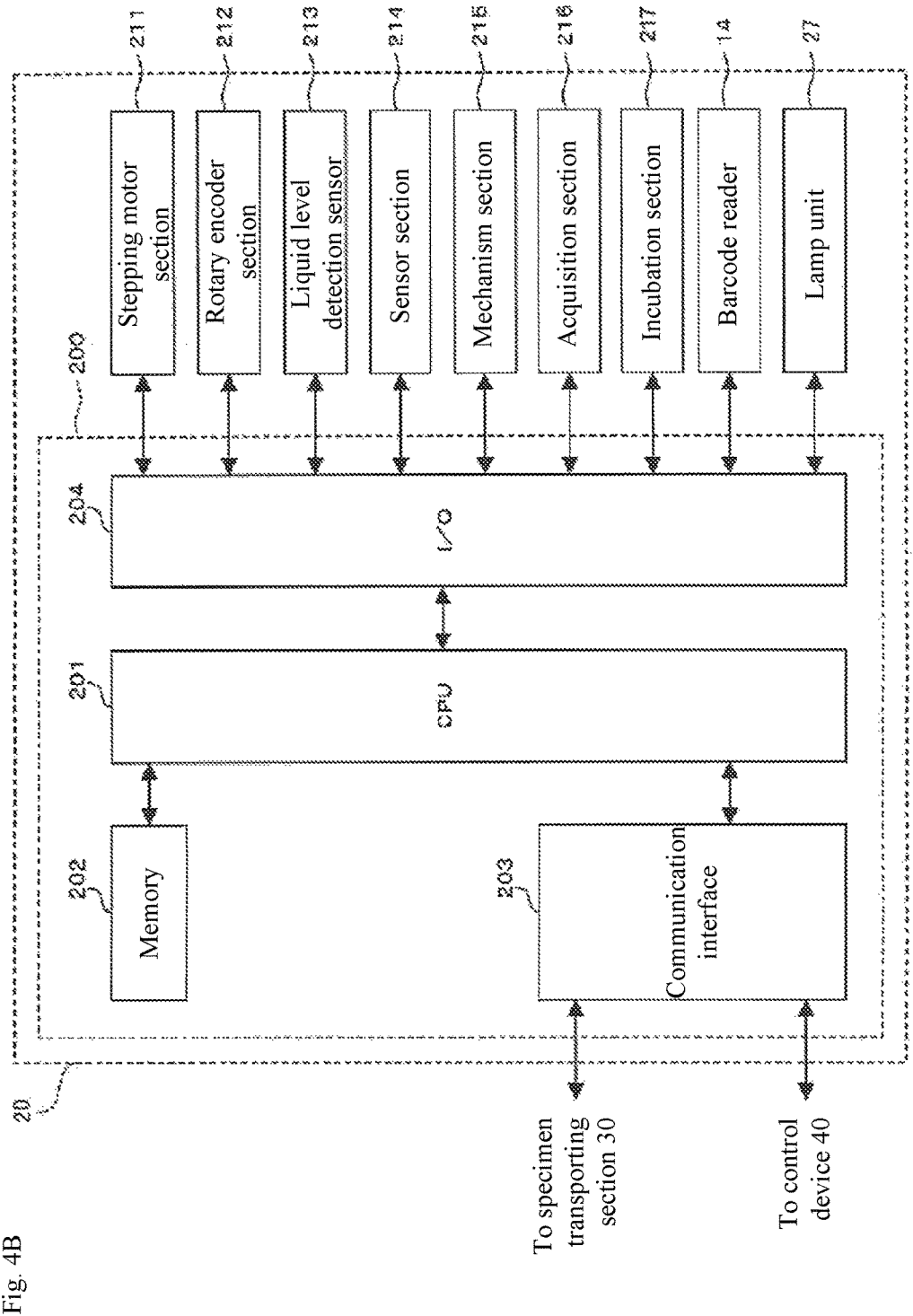
FIG. 4B is a diagram showing a configuration of a measurement device provided in the blood coagulation analyzer according to the third aspect.

In the device according to another embodiment, as shown in FIG. 4B, the measurement unit 20 further includes an incubation section 217. The incubation section 217 incubates the blood specimen of a subject, the normal blood specimen and the mixed specimen under predetermined conditions (for example, 2 hours at 37° C.) in order to measure delayed coagulation time. The incubation section 217 may include the warming section 24 or may include a separately provided warming section (a warming section different from the warming section 24).

The configuration of the control device 40 will be described below. As shown in FIG. 2, the control device 40 includes the display unit 41, an input unit 42, and a computer body 43. The control device 40 receives optical information from the measurement unit 20. Moreover, the processor of the control device 40 calculates coagulation time based on the optical information. Further, the processor of the control device 40 calculates the value of the first quantification index and the value of the second quantification index based on the calculated coagulation time, and the value of ratio or difference between them or the value by combining them. Also, the processor of the control device 40 may execute a computer program for determination of the blood specimen. The control device 40 corresponds to the system for blood coagulation analysis according to the present embodiment.

Figure 7:
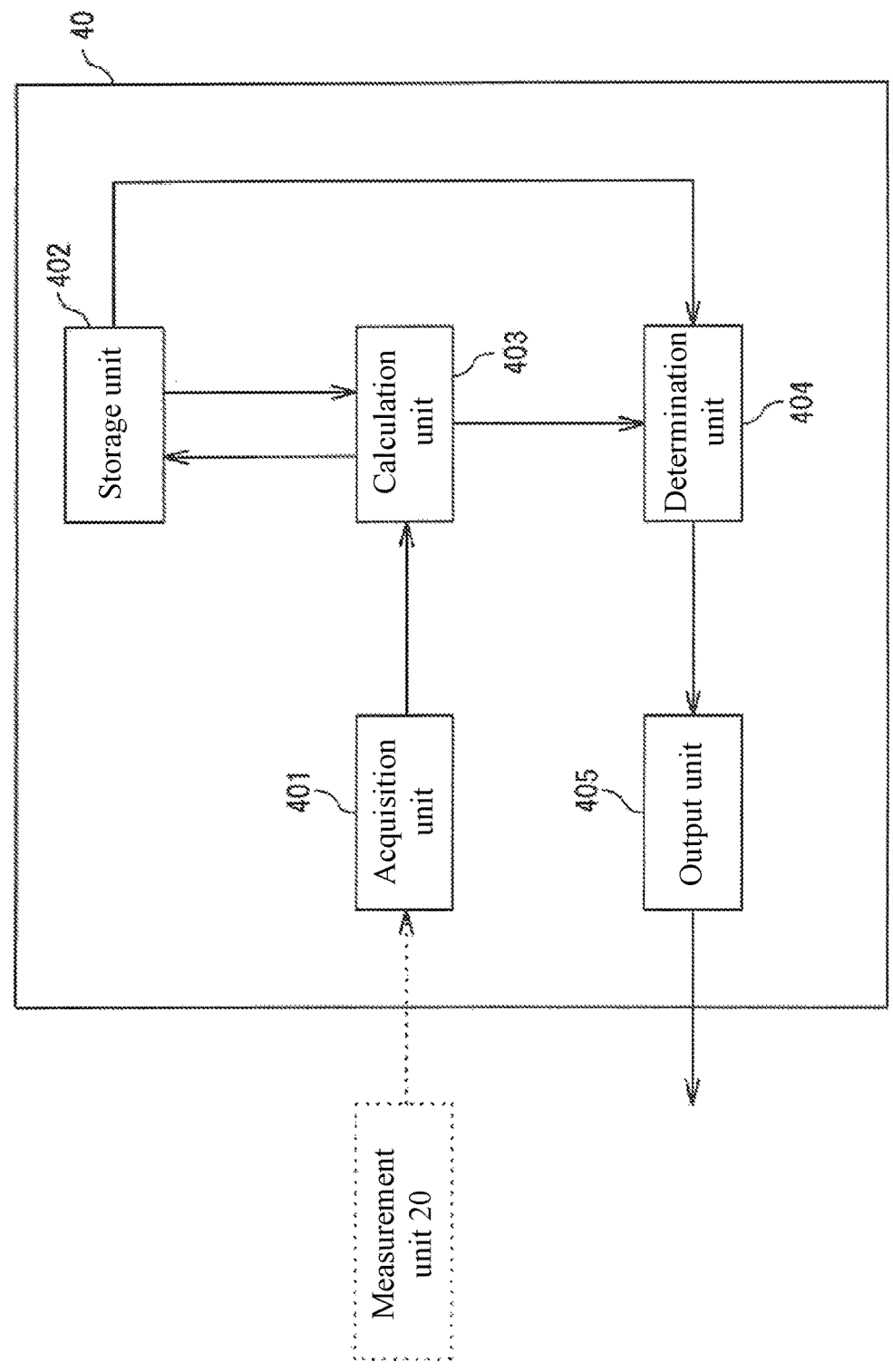
FIG. 7 is a diagram showing a functional configuration of a control device provided in the blood coagulation analyzer.

As to the functional configuration of the control device 40, as shown in FIG. 7, the control device 40 includes an acquisition unit 401, a storage unit 402, a calculation unit 403, a determination unit 404, and an output unit 405. The acquisition unit 401 is communicably connected to the measurement unit 20 via a network. The output unit 405 is communicably connected to the display unit 41.

The acquisition unit 401 acquires the optical information transmitted from the measurement unit 20. The storage unit 402 stores a formula for calculating coagulation time from the optical information, a formula for calculating the value of the first quantification index and the value of the second quantification index from the coagulation time, a formula for executing calculation using the value of the first quantification index and the value of the second quantification index, and the like. Also, the storage unit 402 also stores a first threshold value and a second threshold value necessary for determination. Using the information acquired by the acquisition unit 401, the calculation unit 403 calculates the value of the first quantification index and the value of the second quantification index, and the value of ratio or difference between them or the value by combining them, according to the formula stored in the storage unit 402. The output unit 405 outputs the values calculated by the calculation unit 403, as reference information on the blood specimen.

In the present embodiment, the determination unit 404 may determine whether or not the values calculated by the calculation unit 403 is less than the threshold values stored in the storage unit 402. In this case, the output unit 405 outputs the determination result by the determination unit 404, as reference information on the blood specimen.

Figure 8:
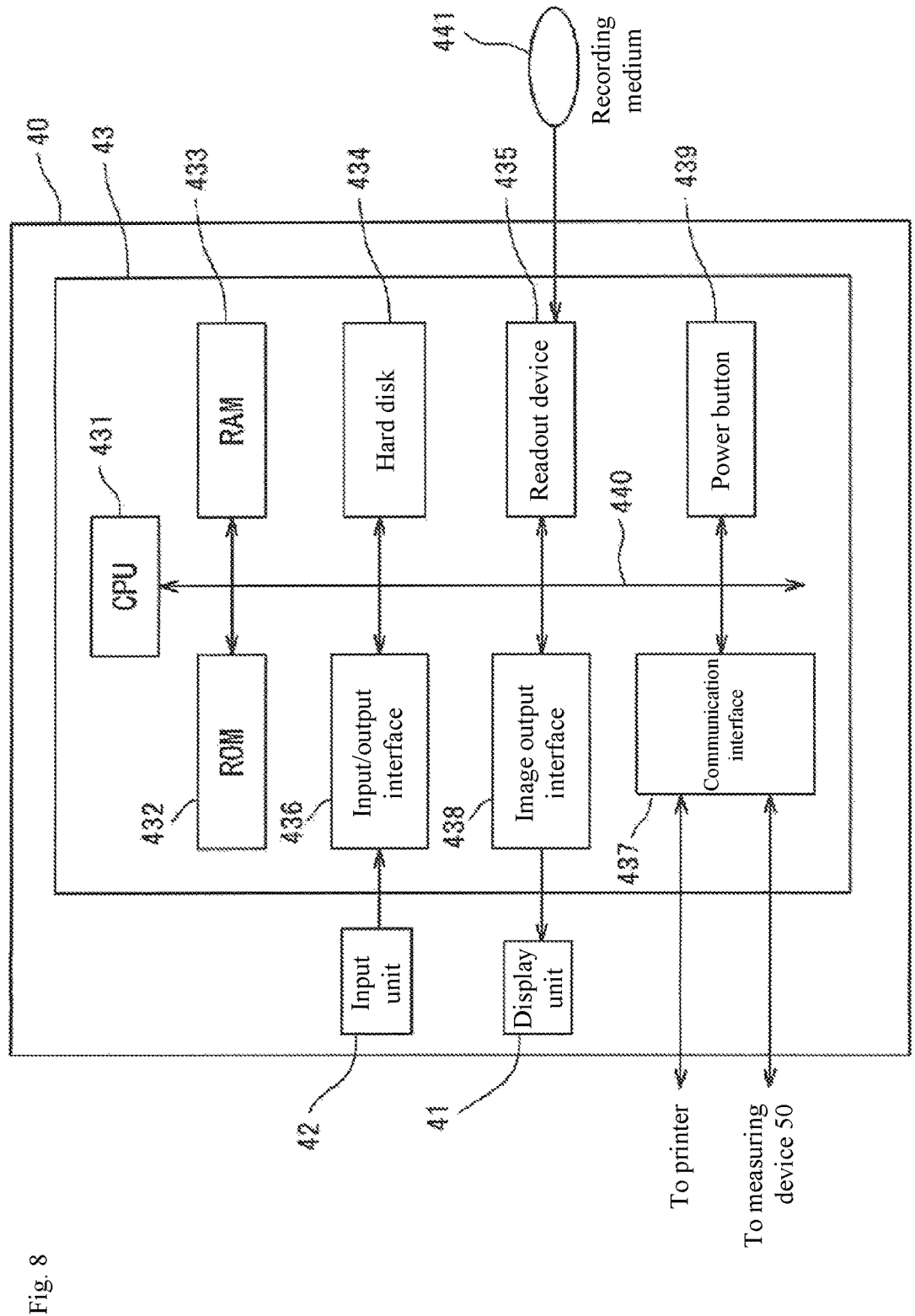
FIG. 8 is a diagram showing a hardware configuration of a control device provided in the blood specimen analyzer.

As shown in FIG. 8, the computer body 43 of the control device 40 includes a CPU 431, a ROM 432, a RAM 433, a hard disk 434, a readout device 435, an input/output interface 436, a communication interface 437, an image output interface 438, and a power button 439. The CPU 431, the ROM 432, the RAM 433, the hard disk 434, the readout device 435, the input/output interface 436, the communication interface 437, the image output interface 438, and the power button 439 are communicably connected by a bus 440.

The CPU 431 executes a computer program stored in the ROM 432 and a computer program loaded in the RAM 433. Each of the above-described functional blocks is realized by the CPU 431 executing an application program. Thus, the computer system functions as a terminal serving as a determination device for determining a blood specimen.

The ROM 432 includes a mask ROM, PROM, EPROM, EEPROM, and the like. In the ROM 432, a computer program executed by the CPU 431 and data used for the computer program are recorded.

The RAM 433 includes SRAM, DRAM, and the like. The RAM 433 is used for reading out the computer program recorded in the ROM 432 and the hard disk 434. The RAM 433 is also used as a work area of the CPU 431 when executing these computer programs.

The hard disk 434 has installed therein an operating system, a computer program such as an application program (a computer program for determination of the blood specimen) to be executed by the CPU 431, data used for executing the computer program, and setting contents of the control device 40.

The readout device 435 includes a flexible disk drive, a CD-ROM drive, a DVD-ROM drive, and the like. The readout device 435 can read out a computer program or data recorded on a portable recording medium 441 such as a CD or a DVD.

The input/output interface 436 includes, for example, a serial interface such as USB, IEEE 1394 or RS-232C, a parallel interface such as SCSI, IDE or IEEE 1284, and an analog interface including a D/A converter, an A/D converter and the like. The input unit 42 such as a keyboard and a mouse is connected to the input/output interface 436. The user inputs an instruction via the input unit 42, and the input/output interface 436 receives a signal input via the input unit 42.

The communication interface 437 is, for example, an Ethernet (registered trademark) interface or the like. The control device 40 can transmit print data to a printer through the communication interface 437. The communication interface 437 is connected to the measurement device 50, and the CPU 431 transmits and receives an instruction signal and data with the measurement device 50 via the communication interface 437.

The image output interface 438 is connected to the display unit 41 including an LCD, a CRT, and the like. The image output interface 438 outputs a video signal corresponding to image data to the display unit 41, and the display unit 41 displays an image based on the video signal output from the image output interface 438.

With reference to FIGS. 4A and 4B, during the measurement operation, the CPU 201 of the measurement unit 20 temporarily stores in the memory 202 the data (optical information) obtained by digitizing the detection signal output from the detecting section 22 (see FIG. 3). The storage area of the memory 202 is divided into areas for each support portion 22a. In each area, the data (optical information) are sequentially stored which are acquired when the cuvette 104 supported by the corresponding support portion 22a is irradiated with light having a predetermined wavelength. Thus, the data is sequentially stored in the memory 202 over a predetermined measurement time. When the measurement time elapses, the CPU 201 stops storing the data in the memory 202, and the CPU 201 transmits the stored data to the control device 40 via the communication interface 203. The control device 40 processes and analyzes the received data. The control device 40 displays the analysis result on the display unit 41.

An example of measurement processing by a device according to the second aspect will be described below, but the present invention is not limited to this example. In this example, immediate coagulation times (first, second and third coagulation times) are measured by the device, and an input of separately measured delayed coagulation times (fourth, fifth and sixth coagulation times) is received, whereby the information on a cause of prolongation of coagulation time for the blood specimen of a subject is outputted. In this example, the delayed coagulation time may be measured by the device according to the above aspect, may be measured by another analyzer, or may be measured by a manual method.

Figure 9A:
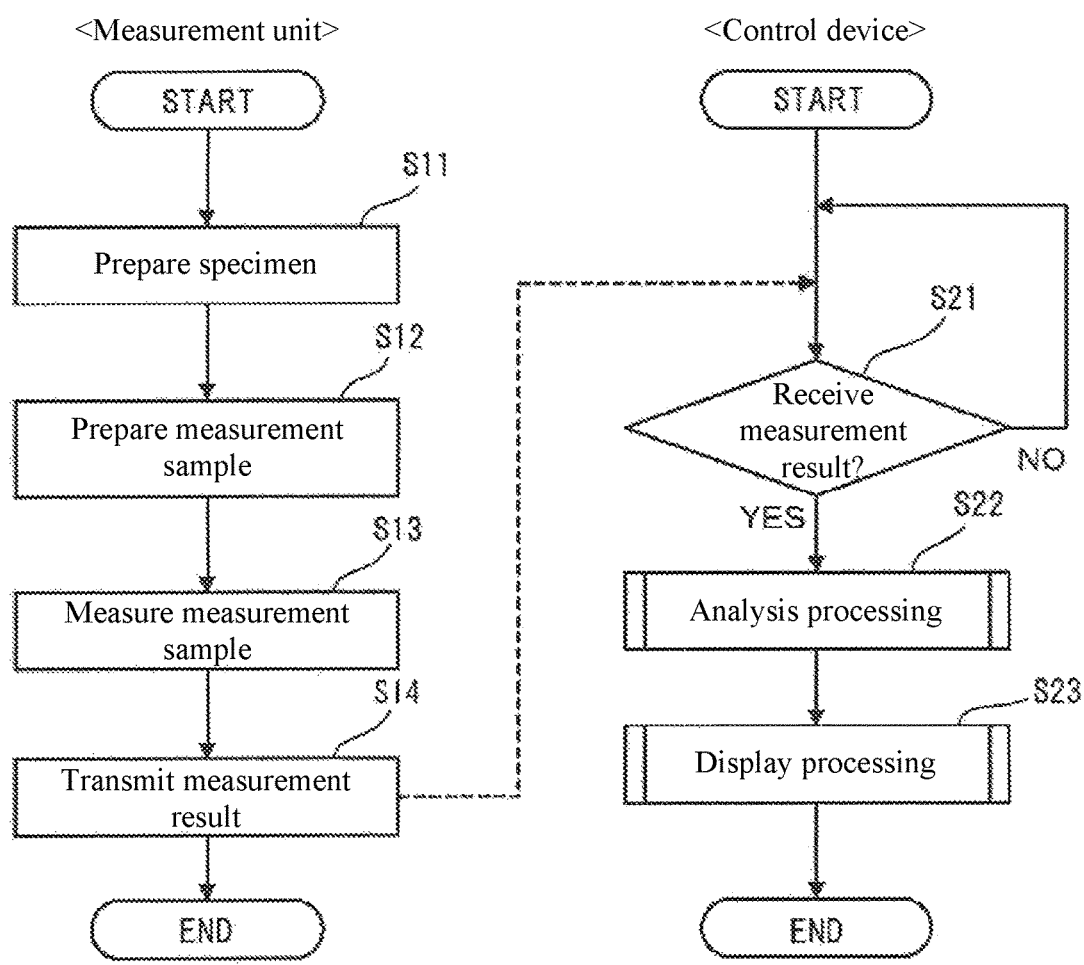
FIG. 9A is a flowchart showing a procedure of preparing and measuring a measurement sample.

The processing in the measurement unit 20 is mainly performed under the control of the CPU 201 of the measurement unit 20, and the processing in the control device 40 is mainly performed under the control of the CPU 431 of the control device 40. With reference to FIG. 9A, when the measurement processing is started, the measurement unit 20 aspirates the blood specimen (plasma) of a subject from the specimen container 101 transported by the specimen transporting section, and the measurement unit 20 dispenses the aspirated blood specimen into an empty cuvette 104 on the cuvette table 13, as described above. Further, the measurement unit 20 aspirates the normal blood specimen (plasma) from the reagent container 103 containing the normal blood specimen accommodated in the reagent accommodating section, and the measurement unit 20 dispenses the aspirated blood specimen into an empty cuvette 104 on the cuvette table 13. Here, the mixed specimen of the blood specimen of a subject and the normal blood specimen may be prepared in advance by the user by a manual method and accommodated in the specimen container 101. Alternatively, the mixed specimen may be prepared by the measurement unit 20. Preparation of the mixed sample by the measurement unit 20 is, for example, as follows. The measurement unit 20 aspirates a predetermined amount of the normal blood specimen (plasma) from the reagent container 103 accommodating the normal blood specimen and dispenses it into an empty cuvette 104. Moreover, the measurement unit 20 aspirates a predetermined amount of the blood specimen (plasma) from the specimen container 101 accommodating the blood specimen of a subject, and dispenses it into the cuvette 104 containing the normal blood specimen, and the mixture is stirred to prepare a mixed specimen.

Subsequently, the measurement unit 20 transfers the cuvettes 104, into which the blood specimen of a subject, the normal blood specimen and the mixed specimen are each dispensed, to the warming section 24, and the blood specimens in the cuvettes 104 are warmed to a predetermined temperature (for example, 37° C.) to prepare each specimen (step S11). Then, the measurement unit 20 adds a reagent to the cuvette 104 to prepare a measurement sample (step S12). The measurement unit 20 starts measuring coagulation time from the time when the reagent is added to the cuvette 104. Thereafter, the measurement unit 20 transfers the cuvette 104 to which the reagent is added to the detecting section 22, and irradiates the cuvette 104 with light to measure the measurement sample (step S13). In this measurement, data (the amount of scattered light or the amount of transmitted light) based on the light with a wavelength of 660 nm is sequentially stored in the memory 202 during the measurement time. At this time, the data is stored in the memory 202 in a state associated with the elapsed time from the reagent addition time point. Then, when the measurement time elapses, the measurement unit 20 stops the measurement, and the measurement unit 20 transmits the measurement result (data) stored in the memory 202 to the control device 40 (step S14).

When the control device 40 receives the measurement result (data) from the measurement unit 20 (step S21: YES), the control device 40 executes analysis processing on the received measurement result (step S22). That is, the control device 40 calculates immediate coagulation times and the first quantification index (for example, ICA, PC or RC-S) for the measurement sample. After performing the analysis processing (step S22), the control device 40 executes the display processing of the analysis result on the specimen in which the immediate coagulation time has been measured (step S23).

Figure 9B:
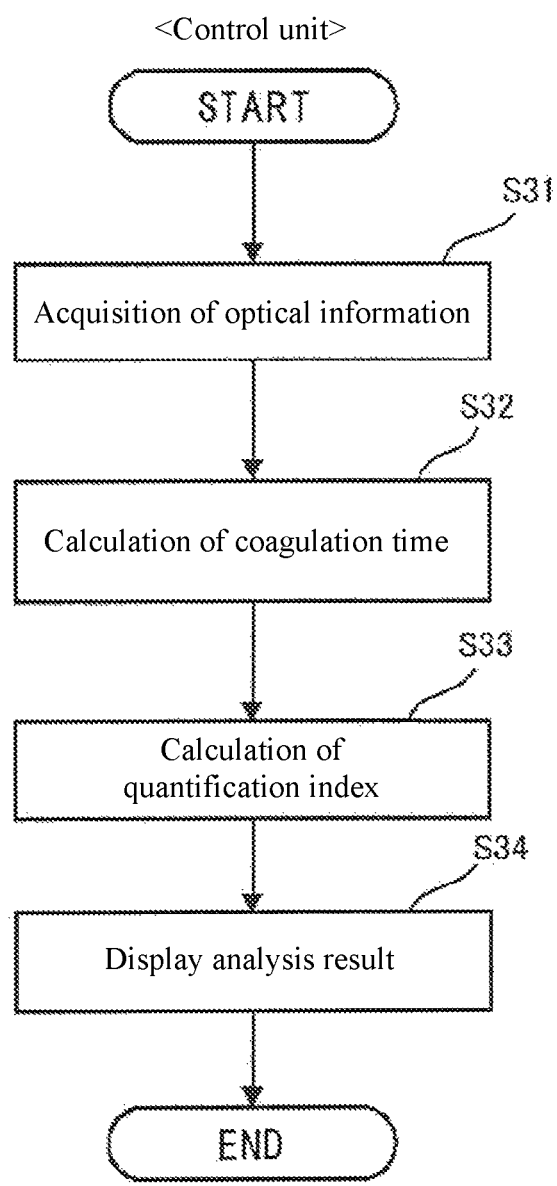
FIG. 9B is a flowchart showing a procedure of analysis processing of measurement data and display processing of analysis result.

The above analysis processing and display processing will be described with reference to FIG. 9B. In step S31, the acquisition unit 401 of the control device 40 acquires optical information (scattered light intensity, or transmittance or absorbance), based on the data (the amount of scattered light or the amount of transmitted light) received from the measurement unit 20. In step S32, the calculation unit 403 calculates immediate coagulation times (first, second, and third coagulation times), from the optical information acquired by the acquisition unit 401, according to the formula for calculating the coagulation time stored in the storage unit 402, and stores the calculated values in the storage unit 402. In step S33, the calculation unit 403 calculates the value of the first quantification index, from the values of the immediate coagulation times stored in the storage unit 402, according to the formula for calculating the quantification index stored in the storage unit 402, and stores the calculated values in the storage unit 402. In step S34, the output unit 405 displays the immediate coagulation times, the first quantification index value, a graph plotting the immediate coagulation time and the like, on the display unit 41, as the analysis results.

When the delayed coagulation time is measured by the device according to the above aspect, each specimen prepared and incubated under predetermined conditions by the user may be measured in the same manner as the above-described measurement of immediate coagulation times.

Subsequently, in the device according to the second aspect, when an input of separately measured delayed coagulation times is received on the screen showing the analysis result for each specimen in which the immediate coagulation time has been measured, the analysis processing and display processing of the information on a cause of prolongation of coagulation time are started. These processing will be described below.

Figure 10:
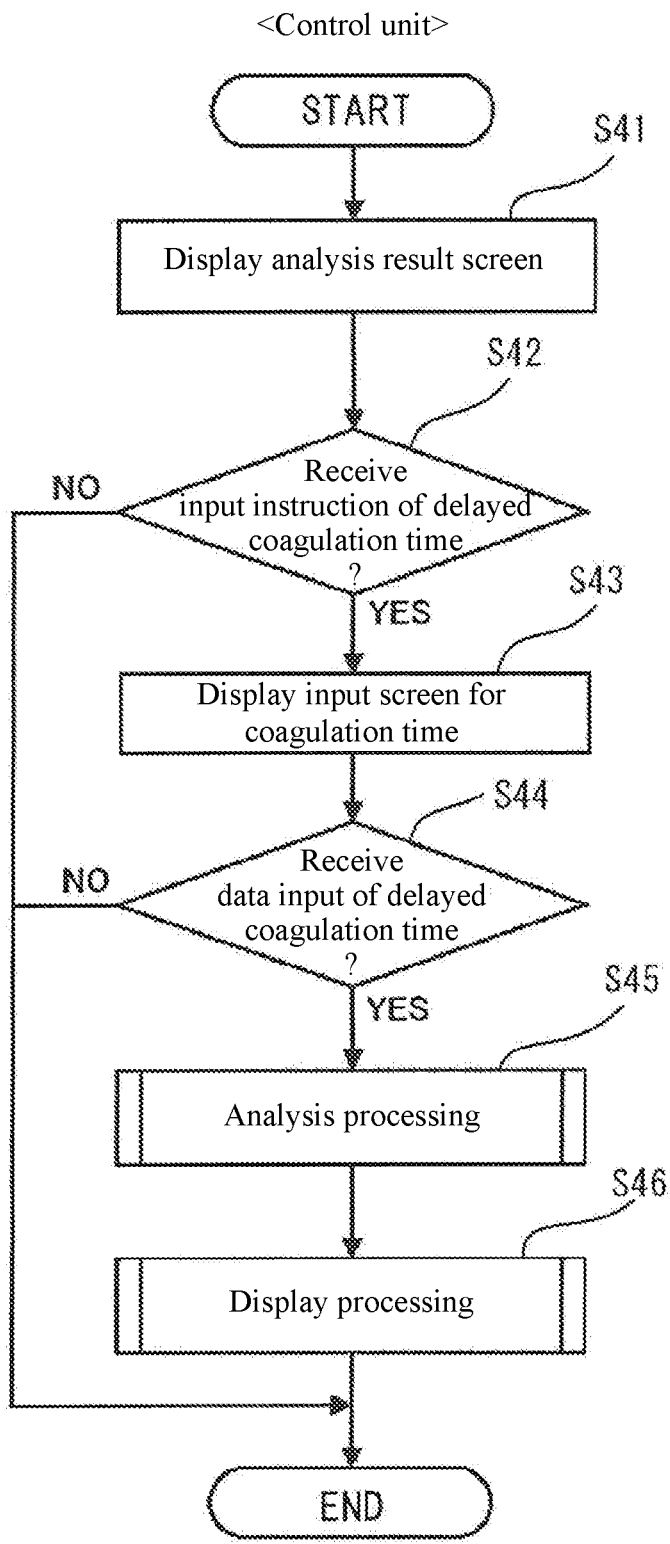
FIG. 10 is a flowchart showing a procedure of input processing of delayed coagulation time.

With reference to FIG. 10, the CPU 431 of the control device 40 receives an input instruction of the delayed coagulation time from the user, in a state of displaying an analysis result screen D1 (FIG. 11A) for each specimen in which the immediate coagulation time has been measured (step S41).

Figure 11A:
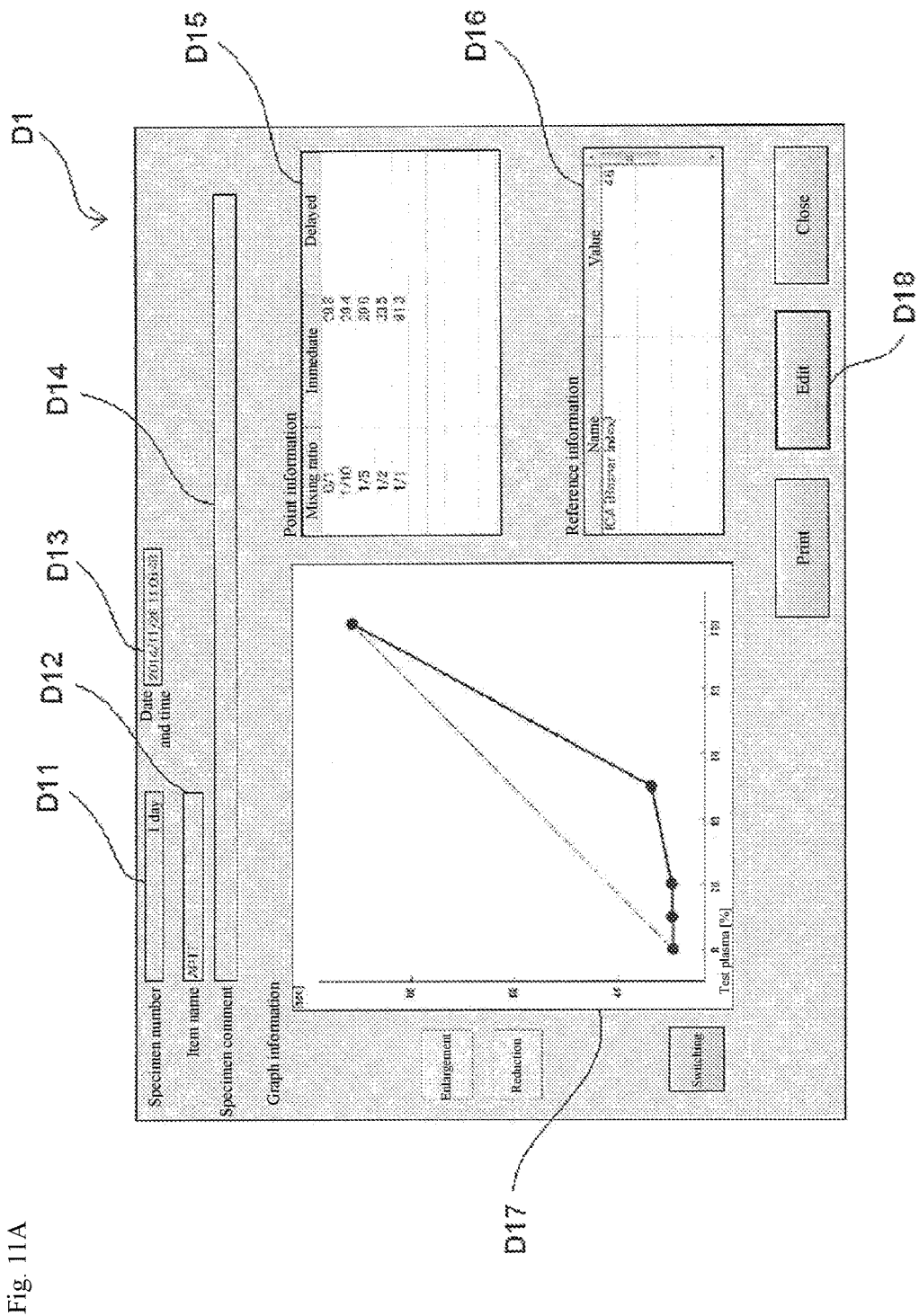
FIG. 11A is a view showing an example of an analysis result screen before inputting delayed coagulation time.

With reference to FIG. 11A, the screen D1 shows a state in which the delayed coagulation time is not inputted. The screen D1 includes an area D11 for displaying a specimen number, an area D12 for displaying a measurement item name, an area D13 for displaying a measurement date and time, an area D14 for displaying a specimen comment, an area D15 for displaying coagulation time and a mixing ratio, an area D16 for displaying reference information, an area D17 for displaying a graph plotting the coagulation time, and a button D18 for displaying an input screen. In FIG. 11A, the mixing ratio and the immediate coagulation time are displayed in the area D15. In the column of the mixing ratio, "0/1" means a normal blood specimen, "1/10", "1/5" and "1/2" mean a mixed specimen with a test plasma ratio of 10, 20 and 50% (v/v), respectively, and "1/1" means a blood specimen of a subject. In FIG. 11A, ICA is displayed as the first quantification index in the area D16.

When the user selects the button D18 on the screen D1, the CPU 431 receives an input instruction of the delayed coagulation time (step S42: YES) and displays an input screen D2 for the delayed coagulation time (FIG. 11B) (step S43). When an input instruction of the second coagulation time is not given (step S42: NO), the CPU 431 terminates the processing.

Figure 11B:
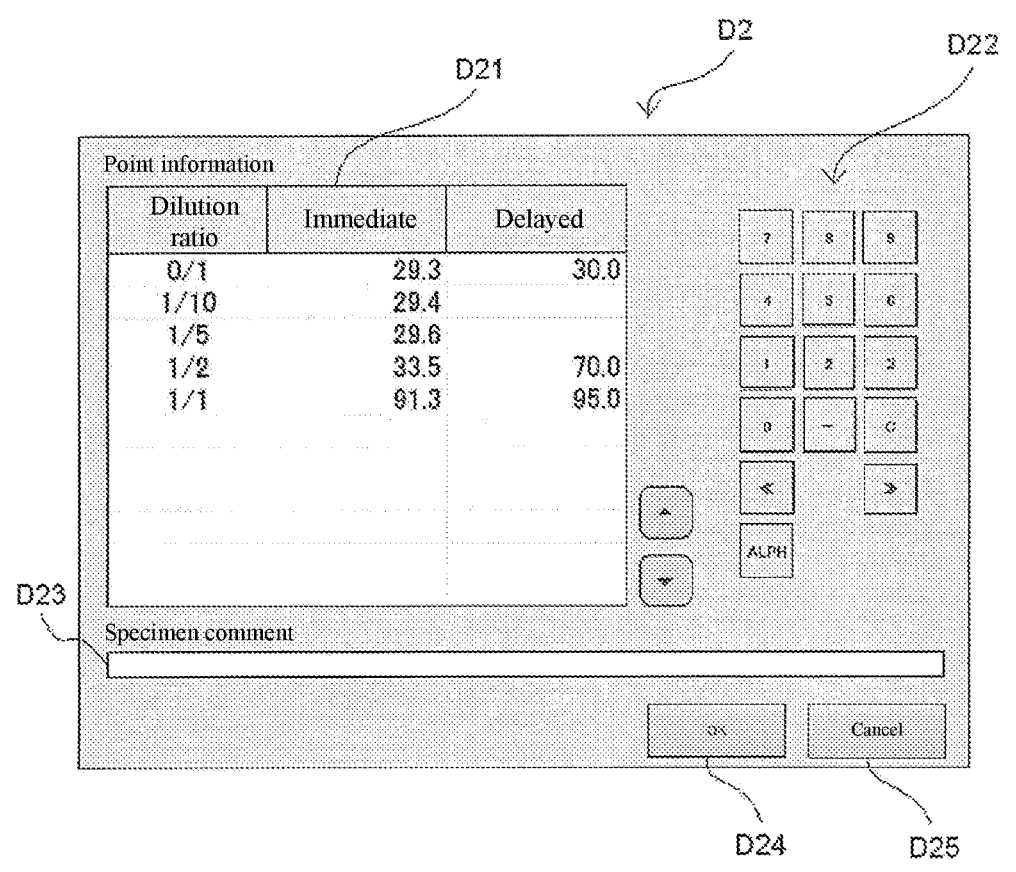

With reference to FIG. 11B, the screen D2 includes an area D21 for displaying a dilution ratio (mixing ratio) of a specimen, immediate coagulation time and delayed coagulation time, a numeric input button D22, an area D23 for displaying a specimen comment, a button D24 for determining an input instruction, and a button D25 for canceling an input instruction. FIG. 11B shows an area D21 after receiving an input of the coagulation time of each of the blood specimen of a subject, the normal blood specimen, and the mixed specimen having a dilution ratio of 1/2, as the delayed coagulation time.

On the screen D2, when the user inputs separately measured delayed coagulation times (fourth, fifth and sixth coagulation times) via the input unit 42 or the numeric input button D22, the CPU 431 receives an input of the delayed coagulation times (step S44: YES), calculates the value of the second quantification index from the delayed coagulation times, and calculates the value of ratio or difference between the value of the first quantification index and the value of the second quantification index (step S45). Alternatively, a value by combining the values of ratio and difference may be calculated. Then, the CPU 431 displays an analysis result screen D3 (FIG. 11C) (step S46). When the delayed coagulation time is not inputted (step S44: NO), the CPU 431 terminates the processing.

Figure 11C:
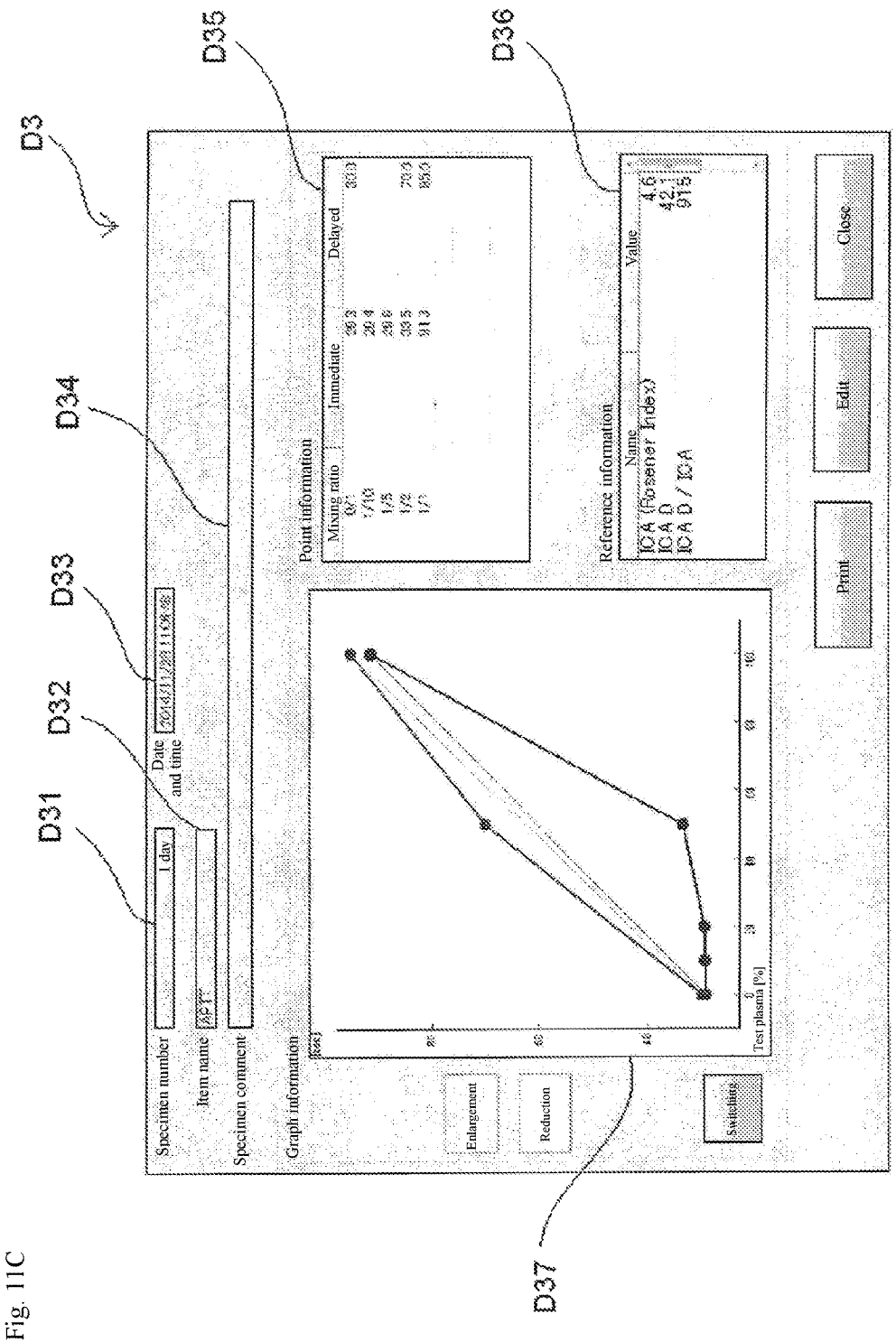
FIG. 11C is a view showing an example of an analysis result screen after inputting delayed coagulation time.

With reference to FIG. 11C, a screen D3 is the screen D1 that has been updated. The screen D3 includes an area D31 for displaying a specimen number, an area D32 for displaying a measurement item name, an area D33 for displaying a measurement date and time, an area D34 for displaying a specimen comment, an area D35 for displaying coagulation time and a mixing ratio, an area D36 for displaying reference information, and an area D37 for displaying a graph plotting the coagulation time. In FIG. 11C, the mixing ratio, the immediate coagulation time, and the delayed coagulation time are displayed in the area D35. In the area D36, ICA calculated from the immediate coagulation time, ICA (ICA D) calculated from the delayed coagulation time, and the ratio between the value of the first quantification index and the value of the second quantification index (ICA D/ICA) are displayed, as the information on a cause of prolongation of coagulation time. In the area D37, a graph plotting each of the immediate coagulation time and the delayed coagulation time is displayed.

An example of measurement processing by a device according to the third aspect will be described below, but the present invention is not limited to this example. In this example, immediate coagulation times (first, second and third coagulation times) and delayed coagulation times (fourth, fifth, and sixth coagulation times) are measured by the device, and the information on a cause of prolongation of coagulation time for the blood specimen of a subject is outputted. That is, in this example, it is not necessary for the user to input the delayed coagulation time.

In this example, the measurement unit 20 prepares at least two sets each of the blood specimen of a subject, the normal blood specimen and the mixed specimen, then, one of which is used as a specimen for measuring immediate coagulation time, and the other is used as a specimen for measuring delayed coagulation time. The measurement process of immediate coagulation time is the same as that described in the measurement process by the device according to the second aspect. The measurement process of delayed coagulation time is the same as the measurement process of immediate coagulation time, except that, in step S11 shown in FIG. 9A, each prepared specimen is incubated under predetermined conditions in the incubation section. Specifically, in step S11, the measurement unit 20 transfers the cuvette 104 into which the blood specimen is dispensed to the incubation section 217, and the blood specimen in the cuvette 104 is incubated under predetermined conditions (for example, at 37° C. for 2 hours).

With reference to FIG. 9A, when the control device 40 receives the measurement result (data) from the measurement unit 20 (step S21: YES), the control device 40 executes analysis processing on the received measurement result (step S22). That is, the control device 40 calculates immediate coagulation time and delayed coagulation time, and the first quantification index and the second quantification index (for example, ICA, PC or RC-S), for the measurement sample. After performing the analysis processing (step S22), the control device 40 executes the display processing of the analysis result for each specimen (step S23).

The above analysis processing and display processing will be described with reference to FIG. 9B. In step S31, the acquisition unit 401 of the control device 40 acquires optical information (scattered light intensity, or transmittance or absorbance), based on the data (the amount of scattered light or the amount of transmitted light) received from the measurement unit 20. In step S32, the calculation unit 403 calculates immediate coagulation times (first, second, and third coagulation times) and delayed coagulation times (fourth, fifth and sixth coagulation times), from the optical information acquired by the acquisition unit 401, according to the formula for calculating the coagulation time stored in the storage unit 402, and stores the calculated values in the storage unit 402. In step S33, the calculation unit 403 calculates the value of the first quantification index and the value of the second quantification index, from each of the values of the immediate coagulation times and delayed coagulation times stored in the storage unit 402, according to the formula for calculating the quantification index stored in the storage unit 402, and stores the calculated values in the storage unit 402. Further, the calculation unit 403 calculates the value of ratio or difference between the value of the first quantification index and the value of the second quantification index, and stores the calculated value in the storage unit 402. Alternatively, a value by combining the values of ratio and difference may be calculated. In step S34, the output unit 405 displays the immediate coagulation times and the delayed coagulation times, the value of the first quantification index and the value of the second quantification index, a graph plotting the immediate coagulation time and the delayed coagulation time and the like, on the display unit 41, as the analysis results. For example, the display unit 41 displays the screen D3 shown in FIG. 11C.

In another embodiment, the control device 40 compares the value of ratio or difference or the value by combining them with the first threshold value, and based on the comparison result, may acquire the information on whether a blood specimen of a subject is suspected of being a specimen containing a coagulation factor inhibitor or suspected of being a specimen having a cause of prolongation other than the coagulation factor inhibitor.

Figure 12A:
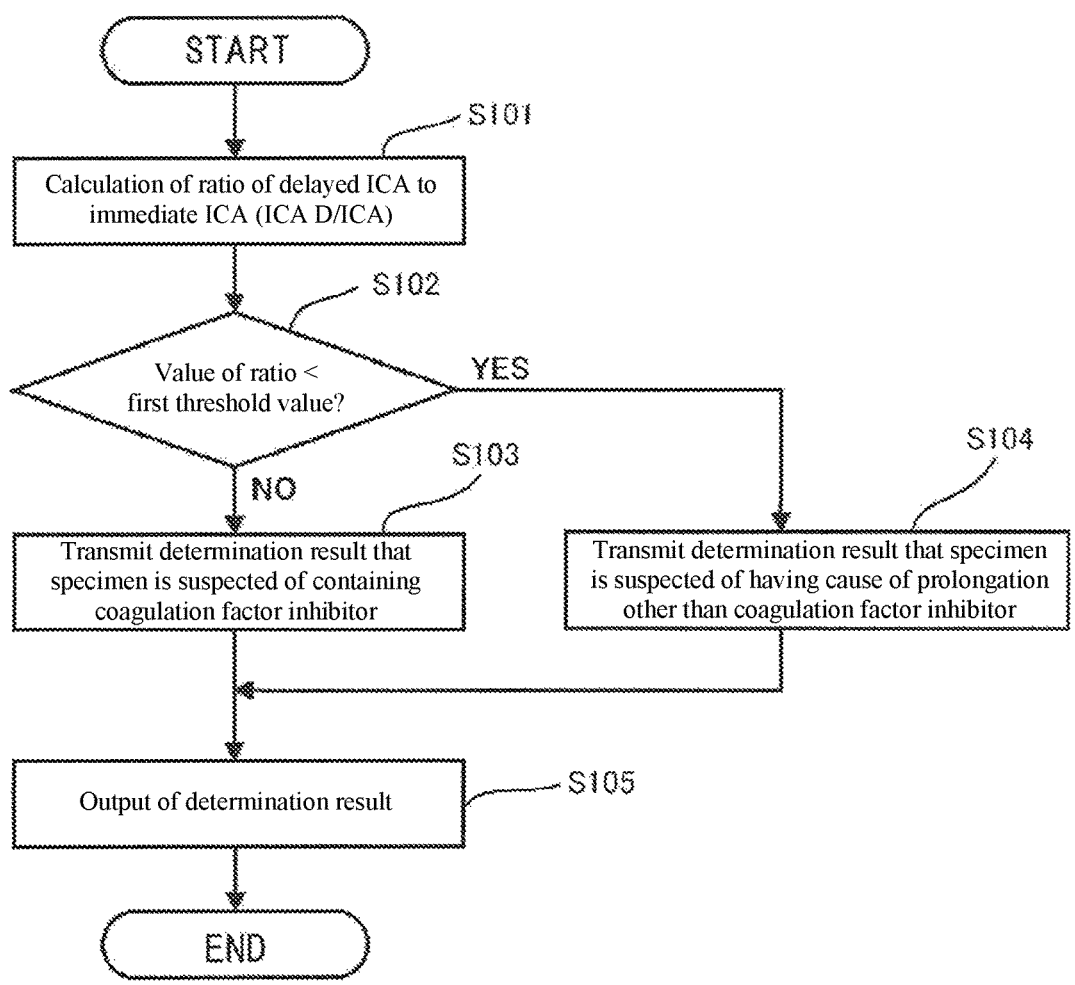
FIG. 12A is a flowchart showing a procedure of determination processing for acquiring information on a coagulation factor inhibitor in the blood specimen.

With reference to FIG. 12A, the flow of determination by the control device will be described below. In FIG. 12A, the case of calculating the value of ratio (ICA D/ICA) from ICA calculated from the immediate coagulation time (hereinafter, also referred to as "immediate ICA") as a first quantification index, and ICA calculated from the delayed coagulation time as a second quantification index (hereinafter, also referred to as "delayed ICA" or "ICA D"), comparing the value of ratio with the first threshold value, and determining the blood specimen will be described as an example. However, the present embodiment is not limited to this example. In this example, PC or RC-S may be used, instead of ICA, and the value of difference, or the value by combining the values of ratio and difference may be used, instead of the value of ratio.

First, in step S101, the calculation unit 403 of the control device 40 calculates the value of ratio between both (ICA D/ICA), using the values of the immediate ICA and delayed ICA stored in the storage unit 402. Next, in step S102, using the value of ratio calculated in the calculation unit 403 and the first threshold value stored in the storage unit 402, the determination unit 404 determines whether the blood specimen of a subject is suspected of being a specimen containing a coagulation factor inhibitor or suspected of being a specimen having a cause of prolongation other than the coagulation factor inhibitor. Here, when the value of ratio is not less than the first threshold value (that is, when the value of ratio is equal to or greater than the first threshold value), the process proceeds to step S103. In step S103, the determination unit 404 transmits to the output unit 405 a determination result that the blood specimen of a subject is suspected of being a specimen containing a coagulation factor inhibitor. On the other hand, when the value of ratio is less than the first threshold value, the process proceeds to step S104. In step S104, the determination unit 404 transmits to the output unit 405 a determination result that the blood specimen is suspected of being a specimen having a cause of prolongation other than the coagulation factor inhibitor.

In step S105, the output unit 405 outputs the determination result, and the output unit 405 displays the determination result on the display unit 41, or the output unit 405 makes a printer to print the determination result. Alternatively, the determination result may be outputted by voice. Thus, the determination result can be provided to the user as reference information on the blood specimen. The reference information on the determination result may be character information or an indicator such as a flag. Further, as the reference information, the first threshold value may be displayed.

In another embodiment, when the control device 40 acquires the information that the blood specimen of a subject is suspected of being a specimen having a cause of prolongation other than the coagulation factor inhibitor, the information on LA in the blood specimen of a subject can be acquired, based on the value of the first quantification index or the second quantification index.

Figure 12B:
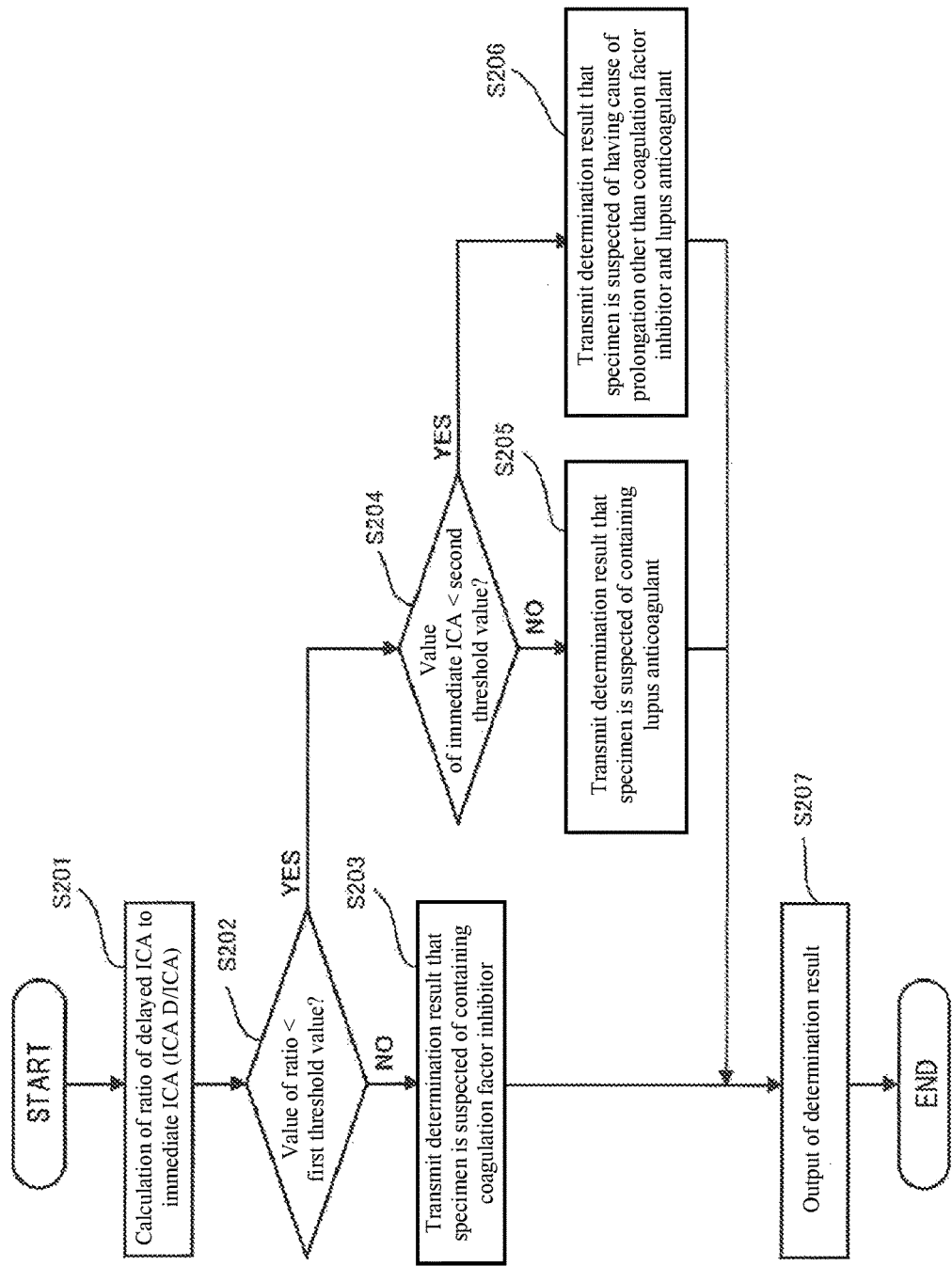
FIG. 12B is a flowchart showing a procedure of determination processing for acquiring information on LA in the blood specimen.

With reference to FIG. 12B, the flow of determination by the control device will be described below. In this flow, the case of comparing the value of immediate ICA with the second threshold value and determining the blood specimen will be described as an example. However, the present embodiment is not limited to this example. In this example, PC or RC-S may be used, instead of ICA, and the value of delayed ICA may be compared with the second threshold value, instead of the value of immediate ICA.

Step 201, step 202 and step 203 shown in FIG. 12B are the same as those described for step 101, step 102 and step 103 in FIG. 12A. In step S202, when the value of ratio between the immediate ICA and the delayed ICA (ICA D/ICA) is less than the first threshold value, the process proceeds to step S204. In step S204, using the value of immediate ICA and the second threshold value stored in the storage unit 402, the determination unit 404 determines whether the blood specimen is suspected of being a specimen containing LA or suspected of being a specimen having a cause of prolongation other than the coagulation factor inhibitor and LA. Here, when the value of immediate ICA is not less than the second threshold (that is, when the value of immediate ICA is equal to or greater than the second threshold value), the process proceeds to step S205. In step S205, the determination unit 404 transmits to the output unit 405 a determination result that the blood specimen of a subject is suspected of being a specimen containing LA. On the other hand, when the value of immediate ICA is less than the second threshold value, the process proceeds to step S206. In step S206, the determination unit 404 transmits to the output unit 405 a determination result that the blood specimen is suspected of being a specimen having a cause of prolongation other than the coagulation factor inhibitor and LA.

In step S207, the output unit 405 outputs the determination result, the output unit 405 displays the determination result on the display unit 41, or the output unit 405 makes a printer to print the determination result. Alternatively, the determination result may be outputted by voice. Thus, the determination result can be provided to the user as reference information on the blood specimen. The reference information on the determination result may be character information or an indicator such as a flag. Further, the first threshold value and the second threshold value may be displayed as the reference information.

Hereinafter, the present invention will be described in more detail with reference to examples, but the present invention is not limited to these examples.

EXAMPLES

Example 1

Based on the value of ratio between the first quantification index and the second quantification index, whether it was possible to differentiate between a coagulation factor inhibitor-positive specimen group and other specimen groups was studied.

(1) Reagents and Specimens

As a coagulation time measuring reagent, Thrombocheck APTT-SLA (Sysmex Corporation) as an APTT reagent, was used. Also, as a calcium solution, a 20 mM calcium chloride solution (Sysmex Corporation) was used. As test plasma, plasma of LA positive patients (15 cases), plasma of coagulation factor (factor V, factor VIII, factor IX or factor XI) deficient patients (17 cases), plasma of heparin-administered patients (8 cases) and plasma of coagulation factor (factor VIII) inhibitor-positive patients (48 cases) were used. As normal plasma, CRYOcheck Pooled Normal Plasma (Precision BioLogic Inc.) was used, and as a control sample for accuracy control, Coagutrol IX•IIX (Sysmex Corporation) was used.

(2) Specimen Processing and Measurement

For each test plasma, test plasma and normal plasma were mixed at a ratio of 1:1 to prepare mixed plasma with a test plasma ratio of 50% (v/v). After preparation of test plasma, normal plasma and mixed plasma, the coagulation time was immediately measured to obtain first, second and third coagulation times (immediate coagulation times). Also, after preparation of test plasma, normal plasma and mixed plasma, they were incubated at 37° C. for 2 hours, and then the coagulation time was measured to obtain fourth, fifth and sixth coagulation times (delayed coagulation times). In the measurement of immediate coagulation times, mixing of the normal plasma and the test plasma and measurement of coagulation times were performed by CS-2400 (Sysmex Corporation). In the measurement of delayed coagulation times, mixing of the normal plasma and the test plasma was performed by a manual method, and the test plasma, the normal plasma and the mixed plasma were incubated at 37° C. for 2 hours, then measurement was performed by CS-2400 (Sysmex Corporation). The specific measurement procedure is as follows. Each plasma was dispensed into a reaction cuvette so that the total volume was 50 μL, and the mixture was warmed at 37° C. for 1 minute. The APTT reagent (50 μL) previously warmed at 37° C. was added thereto, and the mixture was reacted at 37° C. for 3 minutes. Then, a 20 mM calcium chloride solution (50 μL) was mixed, and the transmittance was measured. The coagulation time was calculated from the obtained transmittance.

(3) Calculation of Quantification Index (ICA)

ICA (immediate ICA) for each specimen was calculated from the immediate coagulation time, according to the following formula. Similarly, ICA (delayed ICA) for each specimen was calculated from the delayed coagulation time.

$$ICA=[(b-c)/a]\times 100$$

(in the formula, a: coagulation time of test plasma, b: coagulation time of mixed plasma with a test plasma ratio of 50% (v/v), c: coagulation time of normal plasma)

(4) Calculation of Ratio Between Immediate ICA and Delayed ICA

The ratio between immediate ICA and delayed ICA for each specimen was calculated, according to the following formula.

$$\text{Ratio (\%)}=[(\text{Value of delayed ICA})/(\text{Value of immediate ICA})]\times 100$$

(5) Analysis Results

Figure 13:
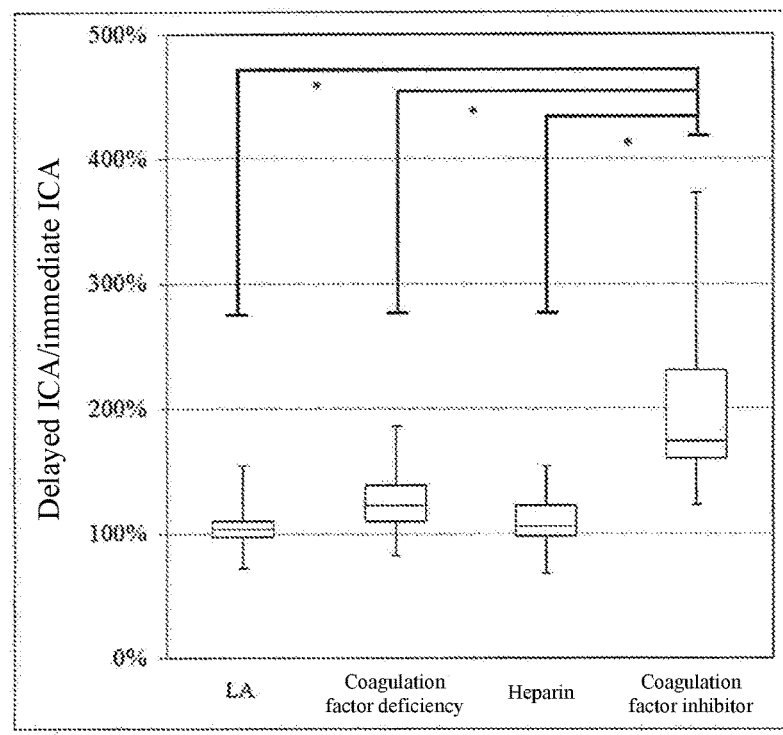
FIG. 13 is a box plot showing the result of analyzing various specimens, based on the value of ratio between the first quantification index and the second quantification index.

A box plot was prepared from the value of ratio between immediate ICA and delayed ICA for each specimen. Comparison between the coagulation factor inhibitor-positive specimen group and each of other specimen groups was performed by Wilcoxon Signed-Rank Test. The results are shown in FIG. 13. In addition, as a result of performing ROC analysis on the coagulation factor inhibitor-positive specimen group, the optimal cutoff value (threshold value) of the ratio between immediate ICA and delayed ICA was 132%. The sensitivity to the coagulation factor inhibitor-positive specimen group when using this cutoff value was 93.8%, and the specificity was 85.0%.

As shown in FIG. 13, the value of ratio for the coagulation factor inhibitor-positive specimen group showed a significant high value as compared with the other specimen groups. In addition, from the results of ROC analysis, the sensitivity and specificity to the coagulation factor inhibitor-positive specimen group were good. Therefore, it is considered that the coagulation factor inhibitor-positive specimen-group and the specimen group having other cause of prolongation can be accurately differentiated, by using the value of ratio between immediate ICA and delayed ICA. Moreover, it is suggested that differentiation from heparin specimen showing APTT prolongation is also possible by using the value of ratio between immediate ICA and delayed ICA.

Example 2

Based on the value of difference between the first quantification index and the second quantification index, whether it was possible to differentiate between a coagulation factor inhibitor-positive specimen group and other specimen groups was studied. In Example 2, the values of immediate ICA and delayed ICA acquired in Example 1 were used.

(1) Calculation of Difference Between Immediate ICA and Delayed ICA

Using the values of immediate ICA and delayed ICA acquired in Example 1, the difference between immediate ICA and delayed ICA for each specimen was calculated, according to the following formula.

$$\text{Difference}=(\text{Value of delayed ICA})-(\text{Value of immediate ICA})$$

(2) Analysis Results

Figure 14:
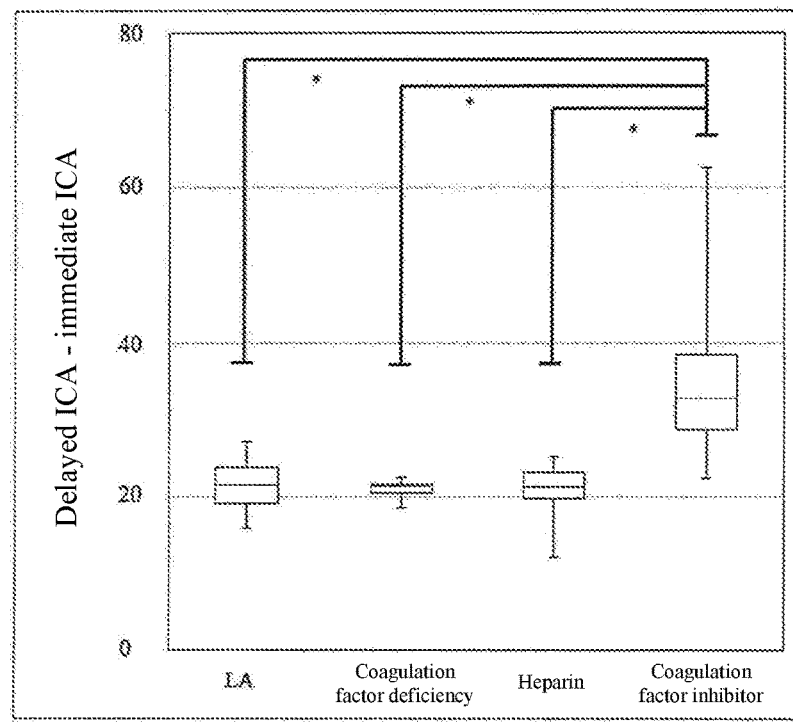
FIG. 14 is a box plot showing the result of analyzing various specimens, based on the value of difference between the first quantification index and the second quantification index.

A box plot was prepared from the value of ratio between immediate ICA and delayed ICA for each specimen. Comparison between the coagulation factor inhibitor-positive specimen group and each of other specimen groups was performed by Wilcoxon Signed-Rank Test. The results are shown in FIG. 14. In addition, as a result of performing ROC analysis on the coagulation factor inhibitor-positive specimen group, the optimal cutoff value (threshold value) of the difference between immediate ICA and delayed ICA was 6.4. The sensitivity to the coagulation factor inhibitor-positive specimen group when using this cutoff value was 91.7%, and the specificity was 98.8%.

As shown in FIG. 14, the value of difference for the coagulation factor inhibitor-positive specimen group showed a significant high value as compared with the other specimen groups. In addition, from the results of ROC analysis, the sensitivity and specificity to the coagulation factor inhibitor-positive specimen group were good. Therefore, it is considered that the coagulation factor inhibitor-positive specimen group and the specimen group having other cause of prolongation can be accurately differentiated, by using the value of difference between immediate ICA and delayed ICA. Moreover, it is suggested that differentiation from heparin specimen showing APTT prolongation is also possible by using the value of difference between immediate ICA and delayed ICA.

Example 3

By using the ratio or difference between immediate ICA and delayed ICA in combination with the value of immediate ICA, whether it was possible to differentiate the disease state was studied. Specifically, the specimens used in Example 1 were classified, based on the following matrix, and the sensitivity and specificity of the classified results were examined. In Example 3, the cutoff value (threshold value) of the ratio between immediate ICA and delayed ICA was set to 132%, the cutoff value (threshold value) of the difference between immediate ICA and delayed ICA was set to 6.4, and the cutoff value (threshold value) of immediate ICA was set to 12.4.

TABLE 1

|  | Delayed ICA/immediate ICA of 132% or more | Delayed ICA/immediate ICA of less than 132% |
| --- | --- | --- |
| Immediate ICA of 12.4 or more | Coagulation factor inhibitor | LA |
| Immediate ICA of less than 12.4 | Coagulation factor inhibitor | Specimen group other than coagulation factor inhibitor and LA |

As a result of using the matrix shown in Table 1, the sensitivity to the LA-positive specimen was 92.6%, and the specificity was 82.2%. Also, the sensitivity to the coagulation factor inhibitor-positive specimen was 93.8%, and the specificity was 85.0%.

TABLE 2

|  | Delayed ICA - immediate ICA of 6.4 or more | Delayed ICA - immediate ICA of less than 6.4 |
| --- | --- | --- |
| Immediate ICA of 12.4 or more | Coagulation factor inhibitor | LA |
| Immediate ICA of less than 12.4 | Coagulation factor inhibitor | Specimen group other than coagulation factor inhibitor and LA |

As a result of using the matrix shown in Table 2, the sensitivity to the LA-positive specimen was 92.6%, and the specificity was 82.2%. Also, the sensitivity to the coagulation factor inhibitor-positive specimen was 91.7%, and the specificity was 98.8%.

Therefore, it was shown that the four specimen groups used in Example 1 can be classified into the coagulation factor inhibitor group, the LA group, and the group having a cause of prolongation other than these, by using the ratio or difference between immediate ICA and delayed ICA in combination with the value of immediate ICA.

Comparative Example

Based on any one value of immediate ICA and delayed ICA, whether it was possible to differentiate between a coagulation factor inhibitor-positive specimen group and other specimen groups was studied. In this comparative example, the values of immediate ICA and delayed ICA acquired in Example 1 were used.

Figure 15A:
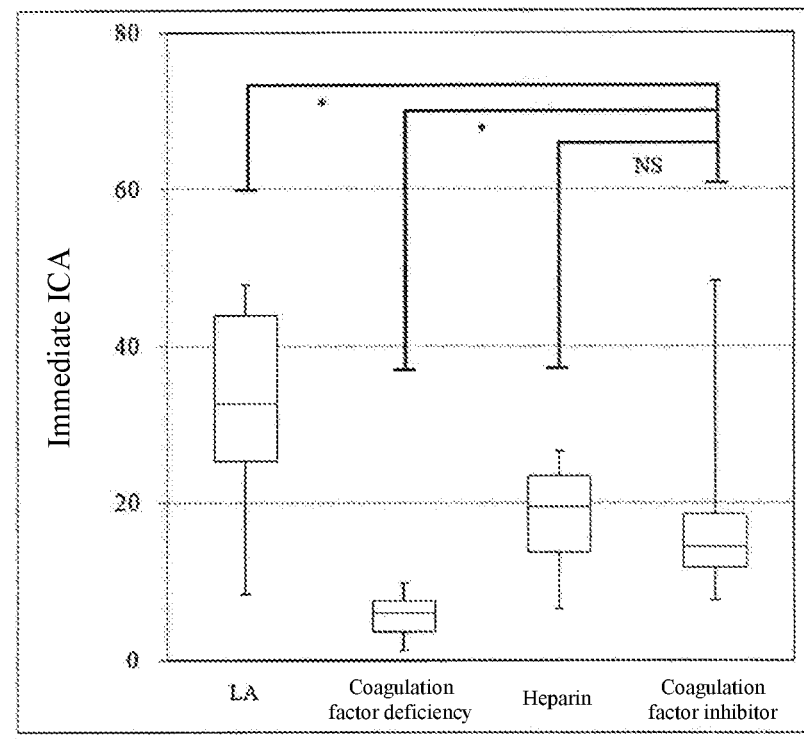
FIG. 15A is a box plot showing a result of analyzing various specimens, based only on the first quantification index.
Figure 15B:
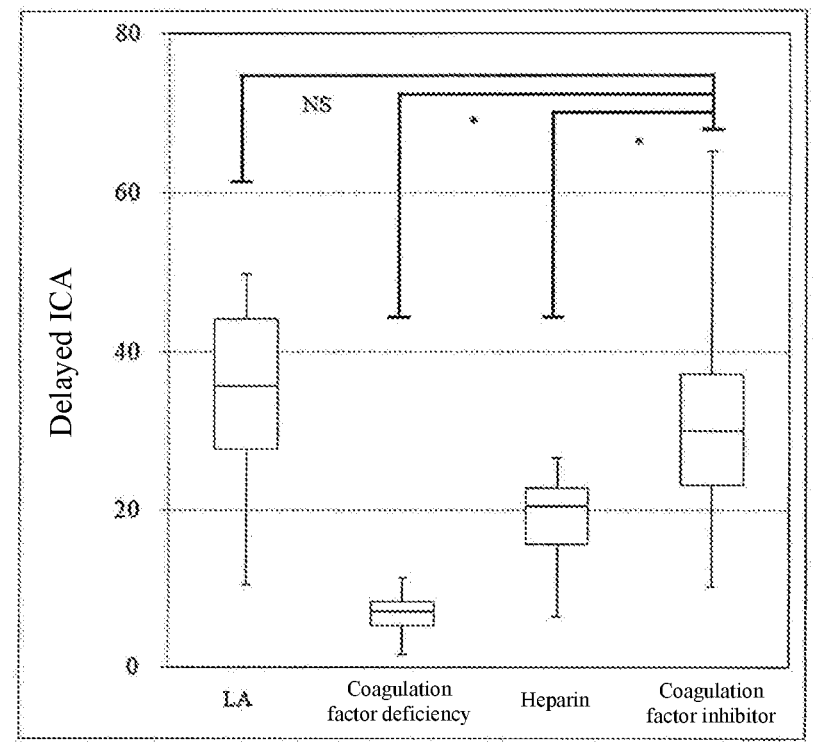
FIG. 15B is a box plot showing a result of analyzing various specimens, based only on the second quantification index.

A box plot was prepared from each of the values of immediate ICA and delayed ICA for each specimen. Comparison between the coagulation factor inhibitor-positive specimen group and each of other specimen groups was performed by Wilcoxon Signed-Rank Test. The results are shown in FIGS. 15A and 15B. As a result of performing ROC analysis on the coagulation factor inhibitor-positive specimen group, the optimal cutoff value of immediate ICA was 11.0 The sensitivity to the coagulation factor inhibitor-positive specimen group when using this cutoff value was 87.5%, and the specificity was 45.0%. Also, the optimal cutoff value of delayed ICA was 23.0. The sensitivity to the coagulation factor inhibitor-positive specimen group when using this cutoff value was 81.3%, and the specificity was 66.3%.

As shown in FIG. 15A, the value of immediate ICA for the coagulation factor inhibitor-positive specimen group was found to be significantly different from that of the LA-positive specimen group and the coagulation factor-deficient specimen group, but no significant difference was observed in comparison with that of the heparin specimen group. Also, as shown in FIG. 15B, the value of delayed ICA for the coagulation factor inhibitor-positive specimen group was found to be significantly different from that of the heparin specimen group and the coagulation factor-deficient specimen group, but no significant difference was observed in comparison with that of the LA-positive specimen group. Therefore, it was shown that it is difficult to separate the coagulation factor inhibitor-positive specimen group from other specimen groups even when the value of immediate ICA or delayed ICA is used alone.

This application is related to Japanese Patent Application No. 2015-39006 filed on Mar. 13, 2015, the claims, the specification, the drawings and the abstract are all incorporated herein by reference.

What is claimed is:

1. A method for acquiring information on a cause of prolongation of coagulation time, the method comprising:
    measuring a first coagulation time of a blood specimen of a subject, a second coagulation time of a normal blood specimen, and a third coagulation time of a mixed specimen in which the blood specimen of the subject and the normal blood specimen are mixed, with a coagulation time measuring reagent;
    measuring a fourth coagulation time of the blood specimen of the subject after incubating the blood specimen of the subject, a fifth coagulation time of the normal blood specimen after incubating the normal blood specimen, and a sixth coagulation time of the mixed specimen after incubating the mixed specimen with the reagent;
    acquiring a first quantification index based on the first, second and third coagulation times, and acquiring a second quantification index based on the fourth, fifth and sixth coagulation times, wherein the first quantification index and the second quantification index are any one selected from an Index of Circulating Anticoagulant (ICA), a Percent Correction (PC), and a Response Curve-Score (RC-S), respectively; and
    the calculating a value of a ratio or a difference between a value of the first quantification index and a value of the second quantification index or a value obtained by combining the value of ratio and the value of difference, and acquiring a calculation result as the information on the cause of prolongation of coagulation time.

2. The method according to claim 1, wherein the first quantification index is an index for quantitatively evaluating a result of a cross mixing test, based on one or all of the first coagulation time, the second coagulation time and the third coagulation time, and the second quantification index is an index for quantitatively evaluating a result of a cross mixing test, based on one or all of the fourth coagulation time, the fifth coagulation time and the sixth coagulation time.

3. The method according to claim 1, further comprising acquiring information on a coagulation factor inhibitor in the blood specimen of the subject, based on the information on the cause of prolongation of the coagulation time.

4. The method according to claim 3, wherein acquiring information on a coagulation factor inhibitor includes comparing the value of the ratio or the difference between the value of the first quantification index and the value of the second quantification index, or the value obtained by combining the value of the ratio and the value of the difference, with a first threshold value, and based on a comparison result, acquiring information on whether the blood specimen of the subject is suspected of being a specimen containing the coagulation factor inhibitor or suspected of being a specimen having a cause of prolongation other than the coagulation factor inhibitor.

5. The method according to claim 4, wherein the value of the ratio is a value obtained by dividing the value of the second quantification index by the value of the first quantification index, and when the value of the ratio is equal to or greater than the first threshold value, the information is acquired that the blood specimen of the subject is suspected of being a specimen containing the coagulation factor inhibitor, and when the value of the ratio is less than the first threshold value, the information is acquired that the blood specimen of the subject is suspected of being a specimen having a cause of prolongation other than the coagulation factor inhibitor.

6. The method according to claim 4, wherein the value of the difference is a value obtained by subtracting the value of the first quantification index from the value of the second quantification index, and when the value of the difference is equal to or greater than the first threshold value, the information is acquired that the blood specimen of the subject is suspected of being a specimen containing the coagulation factor inhibitor, and when the value of difference is less than the first threshold value, the information is acquired that the blood specimen of the subject is suspected of being a specimen having a cause of prolongation other than the coagulation factor inhibitor.

7. The method according to claim 4, wherein when the information is acquired that the blood specimen of the subject is suspected of being a specimen having a cause of prolongation of coagulation time other than the coagulation factor inhibitor, the method further comprises acquiring information on a lupus anticoagulant in the blood specimen of the subject based on the value of the first quantification index or the second quantification index.

8. The method according to claim 7, wherein during acquiring information on a lupus anticoagulant, when one value selected from the first quantification index and the second quantification index is compared with a second threshold value, and the value of the selected quantification index is equal to or greater than the second threshold value, information is acquired that the blood specimen of the subject is suspected of being a specimen containing a lupus anticoagulant, and when the value of the selected quantification index is less than the second threshold value, information is acquired that the blood specimen of the subject is suspected of being a specimen having a cause of prolongation of coagulation time other than the coagulation factor inhibitor and the lupus anticoagulant.

9. The method according to claim 1, wherein the coagulation time measuring reagent is a reagent for measuring at least one selected from the group consisting of a prothrombin time, an activated partial thromboplastin time, a dilute prothrombin time, a dilute activated partial thromboplastin time, a kaolin clotting time, a dilute Russell viper venom time, a thrombin time, and a dilute thrombin time.

10. The method according to claim 1, wherein the blood specimen of the subject is whole blood or plasma.

11. The method according to claim 1, wherein incubating the blood specimen of the subject, the normal blood specimen and the mixed specimen when measuring the fourth, fifth and sixth coagulation times comprises incubating the specimens at 15° C. to 40° C. for 45 minutes to 4 hours.

* * * * *